United States Patent
Giol et al.

(10) Patent No.: US 11,192,977 B2
(45) Date of Patent: Dec. 7, 2021

(54) USE OF POLY(ALKYLENE TEREPHTHALATES) AND METHODS FOR THEIR PREPARATION

(71) Applicant: UNIVERSITEIT GENT, Ghent (BE)

(72) Inventors: Elena Diana Giol, Brasov (RO); Peter Dubruel, Ghent (BE); Sandra Van Vlierberghe, Sint-Niklaas (BE)

(73) Assignee: UNIVERSITEIT GENT, Ghent (BE)

( * ) Notice: Subject to any disclaimer, the term of this patent is extended or adjusted under 35 U.S.C. 154(b) by 337 days.

(21) Appl. No.: 16/082,844

(22) PCT Filed: Mar. 23, 2017

(86) PCT No.: PCT/EP2017/056989
§ 371 (c)(1),
(2) Date: Sep. 6, 2018

(87) PCT Pub. No.: WO2017/162823
PCT Pub. Date: Sep. 28, 2017

(65) Prior Publication Data
US 2019/0031824 A1 Jan. 31, 2019

(30) Foreign Application Priority Data
Mar. 23, 2016 (EP) ..................................... 16161914

(51) Int. Cl.
| | |
|---|---|
| C08G 63/183 | (2006.01) |
| A61L 27/18 | (2006.01) |
| A61L 27/38 | (2006.01) |
| A61L 27/50 | (2006.01) |
| A61L 27/54 | (2006.01) |
| A61L 27/58 | (2006.01) |
| C08G 63/81 | (2006.01) |
| C12N 5/00 | (2006.01) |
| C12N 5/071 | (2010.01) |
| C12M 1/32 | (2006.01) |
| C12M 1/00 | (2006.01) |

(52) U.S. Cl.
CPC ............ *C08G 63/183* (2013.01); *A61L 27/18* (2013.01); *A61L 27/3808* (2013.01); *A61L 27/3895* (2013.01); *A61L 27/507* (2013.01); *A61L 27/54* (2013.01); *A61L 27/58* (2013.01); *C08G 63/81* (2013.01); *C12M 23/12* (2013.01); *C12M 23/20* (2013.01); *C12M 47/04* (2013.01); *C12N 5/0068* (2013.01); *C12N 5/069* (2013.01); *A61L 2300/64* (2013.01); *C08G 2230/00* (2013.01); *C12N 2533/30* (2013.01)

(58) Field of Classification Search
None
See application file for complete search history.

(56) References Cited

U.S. PATENT DOCUMENTS

| | | | | |
|---|---|---|---|---|
| 4,066,627 | A * | 1/1978 | Borman | ............... C08G 63/183 |
| | | | | 528/279 |
| 5,545,212 | A * | 8/1996 | Wakabayashi | ............ A61F 2/06 |
| | | | | 623/1.32 |
| 7,767,781 | B2 | 8/2010 | Phelps et al. | |
| 2014/0296471 | A1 * | 10/2014 | Ito | ........................... C07C 31/20 |
| | | | | 528/272 |
| 2015/0087789 | A1 | 3/2015 | Utsunomiya et al. | |
| 2016/0058588 | A1 * | 3/2016 | Yamada | ................ A61L 33/068 |
| | | | | 623/1.16 |

FOREIGN PATENT DOCUMENTS

| | | | |
|---|---|---|---|
| CH | 331409 A | 7/1958 | |
| WO | WO-2015077300 A1 * | 5/2015 | ........... A61K 9/1635 |
| WO | 2017051912 A1 | 3/2017 | |

OTHER PUBLICATIONS

Chen et al. "Preparation and characterization of aliphatic/aromatic copolyesters based on bisphenol-A terephthalate, hexylene terephthalate and lactide mioties." Reactive and Functional Polymers 67.5 (2007): 396-407 (Year: 2007).*

Koller et al. (1998) "Tissue culture surface characteristics influence the expansion of human bone marrow cells," Biomaterials, 19(21):1963-1972.

International Preliminary Report on Patentability for International Application No. PCT/EP2017/056989, dated Sep. 25, 2018.

* cited by examiner

*Primary Examiner* — Emily A Cordas
(74) *Attorney, Agent, or Firm* — Lathrop GPM LLP; James H. Velema, Esq.

(57) ABSTRACT

The present invention relates to poly(alkylene terephthalate) polyesters having long poly-methylene segments and their use in a wide variety of applications. Particularly, said PAT polyesters are used in biotechnological or biomedical applications, wherein the extent of cell adhesion, cell growth or cell interaction, in particular endothelial cells, depends on the odd or even number of carbon atoms in the aliphatic segments. Also provided are methods for the preparation of poly(alkylene terephthalates) (PAT) having long poly-methylene segments, wherein the bifunctional monomers, in particular terephthalic acid (or a derivative thereof) and an aliphatic diol, are dissolved in a solvent and the polycondensation reaction takes place in solution.

20 Claims, 7 Drawing Sheets

USE OF POLY(ALKYLENE TEREPHTHALATES) AND METHODS FOR THEIR PREPARATION

RELATED APPLICATIONS

Figure 1:
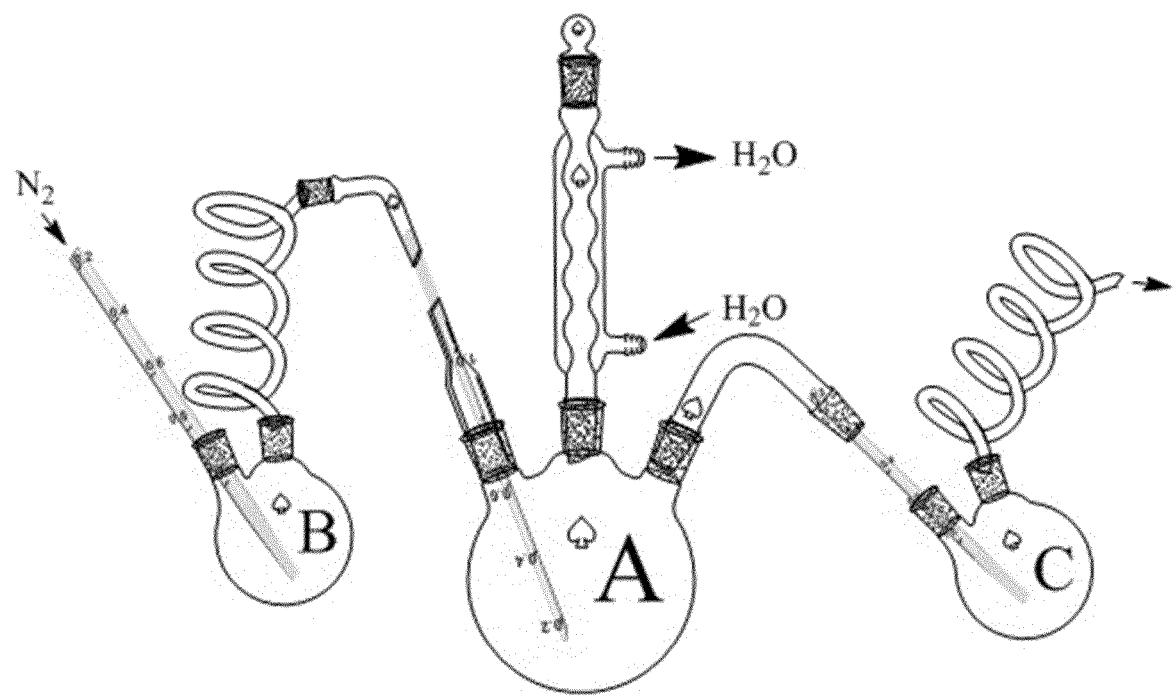

This application is a 35 U.S.C. § 371 filing of International Patent Application No. PCT/EP2017/056989, filed Mar. 23, 2017, which claims the benefit of priority to European Patent Application No. 16161914.3, filed Mar. 23, 2016. The entire contents of these applications are incorporated herein by reference for all purposes.

FIELD OF THE INVENTION

The present invention relates to the field of linear aliphatic-aromatic polyesters, in particular to the preparation and use of linear aromatic PET-like polyesters with long methylene segments, in particular poly(alkylene terephthalate)s.

BACKGROUND TO THE INVENTION

Poly(ethylene terephthalate) or PET is the most common aromatic polyester thermoplastic resin, belonging to the family of poly(alkylene terephthalate)s (PAT) (i.e. polyesters that are polycondensates derived from terephthalic acid or its dialkylester (e.g its dimethylester) and an aliphatic diol, which in the case of PET is ethylene glycol). PET finds widespread use in e.g. fibers for clothing and containers for liquids and food, due to its good bulk properties such as excellent thermal and mechanical properties, inertness and chemical stability. Despite its industrial versatility, PET resins are less suited for certain applications in the medical field due to an insufficient flexibility/distensibility of the material and/or because of its insufficient cell interactive properties. PET with increased flexibility can be obtained by blending it with poly(butylene terephthalate) or butylene glycol; or by incorporation of urethane moieties within the PET backbone. However, in these cases, phase separation occurs (at a microscopic level) mainly due to the high hydrophobicity of the components. Also, surface modification is required to obtain (surface modified) PET substrates with enhanced biocompatibility to which cells, in particular endothelial cells, can adhere and proliferate. For instance, implantable medical devices, such as synthetic vascular grafts or other implants, directly interact with cells. It is thus a requirement that such medical devices sustain cell adhesion and a balanced cell growth in order to have the cells populate the implant.

PAT polyesters, like PET, are typically obtained by melt polycondensation of the monomers at high temperatures (about 250° C.) under vacuum conditions and require catalysts (eg. Ti(OBu)4, tetrabutyl titanate). Often, additives, like heat stabilisers, are added during the melt polycondensation reaction.

There thus remains a need in the art for PET-like polyesters, and the synthesis thereof, which are more flexible and exhibit more biologically relevant characteristics compared to PET, and which can be processed and prepared under more favourable conditions, such as at lower temperatures.

SUMMARY OF THE INVENTION

The inventors have surprisingly found that linear PAT polyesters with long aliphatic segments exhibit a specific, polymer dependent interactivity with endothelial cells. In addition, the inventors have developed novel methods for producing linear PAT polyesters, particularly PAT polyesters with long aliphatic (methylene) segments. This way, one or more of the disadvantages of the prior art detailed above have been addressed.

Indeed, said linear aromatic PAT polyesters, comprising an aliphatic chain of at least four or five methylene ($-CH_2-$) groups, particularly as obtained by the method described herein, exhibit an increased flexibility and can be processed at lower temperatures. Surprisingly, said PAT polyesters comprising an aliphatic chain of at least four or five methylene groups, obtainable by the methods envisaged herein, exhibit cell-interactive properties in particular with endothelial cells, allowing their adhesion and proliferation without requiring additional processing steps (such as blending or surface modification). In addition, the inventors found a specific preference on endothelial cell types, dependent on the odd or even number of carbon atoms making up the aliphatic chain of these PAT polyesters. In particular, (primary) endothelial cells originating from micro- or macrovessels, such as human dermal microvascular endothelial cells (HDMEC) or human umbilical vein endothelial cells (HUVEC), respectively, adhere and proliferate on PAT polyesters containing an even number of carbon atoms, preferably comprising at least four, six, eight or ten methylene groups. Conversely, the odd counterparts, preferably comprising at least five, seven, nine or eleven methylene groups, selectively allow the proliferation of macrovascular endothelial cells, such as HUVECs on their surface and inhibit the adhesion and proliferation of microvascular endothelial cells, such as HDMECs.

In addition, it has been found that the synthesis of linear poly(alkylene terephthalate) polymers, comprising an aliphatic chain of at least two, preferably at least four, methylene ($-CH_2-$) groups, by solution polycondensation, i.e. in the presence of a suitable solvent under mild reaction conditions and in the absence of a catalyst, is a straightforward, highly reproducible, easily scalable method to produce a wide variety of linear aromatic polyesters having a low polydispersity index (PDI), such as a PDI ranging from 1.1 to 2.5. Advantageously, the methods as envisaged herein allow for a better reproducibility of the PAT synthesis and to obtain such polymers in a simple and cost-efficient way and at milder reaction conditions. In contrast to PAT polymers obtained via a two-step melt polycondensation, the present synthesis by solution polycondensation allowed to obtain PAT polymers in the absence of a catalyst, via a one-step process, without the synthesis of intermediate compounds.

The present invention generally relates to methods for producing a PAT polyester polymer, the polyester polymers thus obtained, cell growth support products comprising said polyester polymers and the use of said polyester polymers.

One aspect of the present invention provides a cell growth support product configured for supporting a cell population, preferably an endothelial cell population, comprising a surface for exposure to the cell population during use, wherein said surface comprises a polyester polymer having the structure (A)

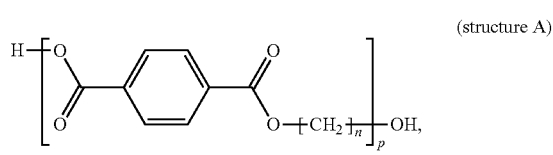

(structure A)

wherein n=4-20 or n=5-20, preferably n=4-12 or n=5-12; and p≥2, preferably p=3 to 100 or more.

Particularly, the cell growth support product for supporting a cell population envisaged herein comprises a polyester polymer having the structure (A) wherein n=4, 6, 8, 10 or 12, and wherein said cell population is a macrovascular endothelial cell population, a microvascular endothelial cell population, or a combination thereof. Alternatively, the cell growth support product for supporting a cell population envisaged herein comprises a polyester polymer having the structure (A) wherein n=5, 7, 9, or 11 and wherein said cell population is a macrovascular endothelial cell population.

In particular embodiments, the cell growth support product envisaged herein and the surface thereof, is made up of said polyester polymer having the structure (A), wherein n=4-20 or n=5-20, preferably n=4-12 or n=5-12; and p≥2, preferably p=3 to 100 or more. Alternatively, the cell growth support product envisaged herein comprises a surface comprising the polyester polymer having the structure (A) in the form of a coating on said cell growth support product.

In particular embodiments, the cell growth support product as envisaged herein is an article, vessel or bioreactor for cell culture applications. In other embodiments, the cell growth support product as envisaged herein is an implantable medical device or a tissue engineering scaffold.

Another aspect of the present invention relates to a method for producing a cell growth support product for supporting a cell population, preferably an endothelial cell population, comprising a surface for exposure to the cell population during use, wherein said surface comprises a polyester polymer having the structure (A)

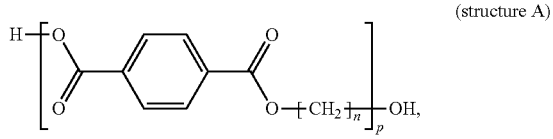
(structure A)

wherein n=4-20 or n=5-20, preferably n=4-12 or n=5-12; and p≥2, preferably p=3 to 100 or more; comprising the steps of:

Obtaining or producing the polyester polymer having the structure (A)

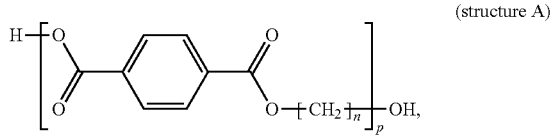
(structure A)

wherein n=4-20 or n=5-20, preferably n=4-12 or n=5-12; and p≥2, preferably p=3 to 100 or more; and subsequently forming said polyester polymer into said cell growth support product.

In certain embodiments, the step of producing the polyester polymer having the structure (A) may comprise any method known in the art, such as via melt polycondensation. In particular embodiments, the step of producing the polyester polymer having the structure (A) comprises the steps of:

(i) mixing a first compound I having the structure of

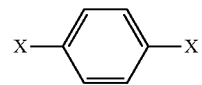

and a second compound II having the structure of Y—$(CH_2)_{n-2}$—Y, wherein n=4-20 or n=5-20, in a solvent, thus obtaining a reaction mixture, wherein X and Y are selected to allow the formation of an ester linkage between compound I and compound II and are selected from the functional moieties —$COR^1$ or —$CH_2OH$ with $R^1$=—$OR^2$ or a halogen, preferable Cl, and $R^2$=H or an alkyl group; and (ii) allowing a polycondensation reaction to proceed in the solvent.

Preferably, the solvent is 1,2-dichlorobenzene or THF. Preferably, an inert gas is passed through the reaction mixture during the reaction step (ii).

Preferably, compound II has the structure $HOCH_2$—$(CH_2)_{n-2}$—$CH_2OH$ and/or wherein compound I has the structure

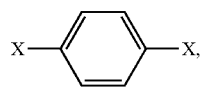

with X=—$COR^1$, where $R^1$=—$OR^2$ or a halogen, preferable Cl, and $R^2$=H or an alkyl group. More preferably, compound I is terephthaloyl chloride and wherein the compound II is 1,5 pentanediol, 1,6 hexanediol, 1,7 heptanediol, 1,8 octanediol, 1,9 nonanediol or 1,10 decanediol.

Another aspect of the present invention relates to a method for expanding an endothelial cell population comprising:
applying endothelial cells to the cell growth support product comprising a polyester polymer having the structure (A) as envisaged herein;
culturing said endothelial cells on said cell growth support product by applying conditions suitable for cell growth.

Said endothelial cell population may comprise macrovascular endothelial cells, microvascular endothelial cells or a combination thereof.

Another aspect of the present invention provides for a method for separating macrovascular and microvascular endothelial cells comprising contacting a cell population comprising macrovascular and microvacular endothelial cells with a cell growth support product as envisaged herein, comprising a polyester polymer having the structure (A), wherein n=5, 7, 9, or 11, and whereby said support product favours adhesion and growth of the macrovascular endothelial cells over the microvascular endothelial cells.

Another aspect of the present invention relates to the use of the cell growth support product as envisaged herein for the growth or production of macrovascular and/or microvascular endothelial cells.

Another aspect of the present invention provides a method for producing a PAT polyester polymer having the structure

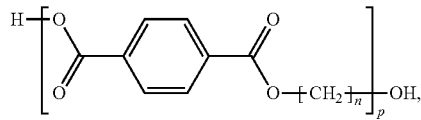

wherein n=2-20; and p≥2, preferably n=4-20 or n=5-20, more preferably n=4-12 or n=5-12 and p=3 to 100 or more; comprising the steps of:
(i) mixing a first compound I having the structure of

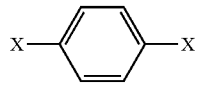

and a second compound II having the structure of Y—(CH$_2$)$_{n-2}$—Y, wherein n=2-20, preferably n=4-20 or n=5-20, more preferably n=4-12 or n=5-12, in a solvent, thus obtaining a reaction mixture, wherein X and Y are selected to allow the formation of an ester linkage between compound I and compound II and are selected from the functional moieties —COR$^1$ or —CH$_2$OH with R$^1$=—OR$^2$ or a halogen, preferable Cl, and R$^2$=H or an alkyl group, and
(ii) allowing a polycondensation reaction to proceed in the solvent.

In particular embodiments of the methods envisaged herein, said solvent is 1,2-dichlorobenzene or THF. In particular embodiments of the methods envisaged herein, an inert gas, such as nitrogen gas or a noble gas, is passed through the reaction mixture during the reaction step (ii). Alternatively, particularly in case an acidic by-product such as HCl or HBr is formed in the polycondensation reaction, an acid capturing agent is used to capture and neutralize said acidic by-product. In particular embodiments of the methods envisaged herein, the first compound I and the second compound II are mixed at a molar ratio ranging from 2:1 to 1:2, preferably at a molar ratio of about 1:1.

In particular embodiments of the methods envisaged herein, said compound II has the structure HOCH$_2$—(CH$_2$)$_{n-2}$—CH$_2$OH and/or wherein compound I has the structure

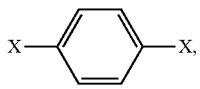

with X=—COR$^1$, wherein R$^1$=—OR$^2$ or a halogen, preferable Cl, and R$^2$=H or an alkyl group. Preferably, said compound I is terephthaloyl chloride. In particular embodiments, said compound I is terephthaloyl chloride, and said compound II is 1,5 pentanediol, 1,6 hexanediol, 1,7 heptanediol, 1,8 octanediol, 1,9 nonanediol or 1,10 decanediol.

Another aspect of the present invention relates to the use of a PAT polyester polymer obtainable by the methods as envisaged herein according to a first aspect of the present invention for preparing fibers, containers or packaging material or in a thermoforming manufacturing process. Another aspect of the present invention relates to the use of a PAT polyester polymer obtainable by the method as envisaged herein for preparing a product configured for medical and biomedical applications. In certain embodiments, said product configured for medical and biomedical applications has cell-interactive properties with endothelial cells or other types of sensitive cells, such as stem cells, but not necessarily limited to these, and is made up of a PAT polyester polymer comprising an aliphatic chain of least four or five methylene groups as envisaged herein. In certain embodiments said PAT polyester has an even number of carbon atoms, preferably 4, 6, 8, 10 or 12 carbon atoms, in its aliphatic chain. In other embodiments, said product configured for medical and biomedical applications presents selective cell interactive properties within endothelial cell types, favouring adhesion of macrovascular endothelial cells over microvascular endothelial cells and wherein said product is made up of a PAT polyester polymer as envisaged herein with an odd number of carbon atoms, preferably with 5, 7, 9 or 11 carbon atoms, in its aliphatic chain.

A particular embodiment of the present invention relates to the use of a PAT polyester polymer having the structure

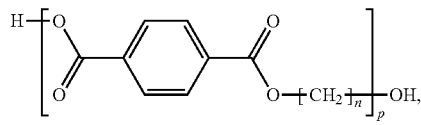

wherein n is ranging from 4 to 20 or from 5 to 20, preferably ranging from 4 to 12 or from 5 to 12 and wherein n is preferably even; and p≥2, preferably p ranging from 3 to 100 or more, for preparing a product having cell interactive properties with macrovascular and microvascular endothelial cells.

Yet another particular embodiment relates to the use of a polyester polymer having the structure

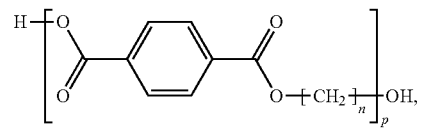

wherein n is odd and ranging from 4 to 20 or from 5 to 20, preferably ranging from 4 to 12 or from 5 to 12; and p≥2, preferably p ranging from 3 to 100 or more, for preparing a product favouring the adhesion of macrovascular endothelial cells over the adhesion of microvascular endothelial cells.

FIGURE LEGENDS

FIG. 1 shows the polycondensation (polyesterification) reaction set-up based on terephthaloyl chloride and an aliphatic diol according to a particular embodiment of the present invention. A three neck round bottom balloon (A) is equipped with an inlet and outlet line of inert gas (N$_2$) and an Allihn condenser. Before entering the reaction mixture, the inert gas is passed through a solvent bath (B) in order to minimize solvent evaporation. The HCl gas by-product is carried away from the reaction mixture by the inert gas and is neutralized in a NaOH collection bath (C).

Figure 2A:
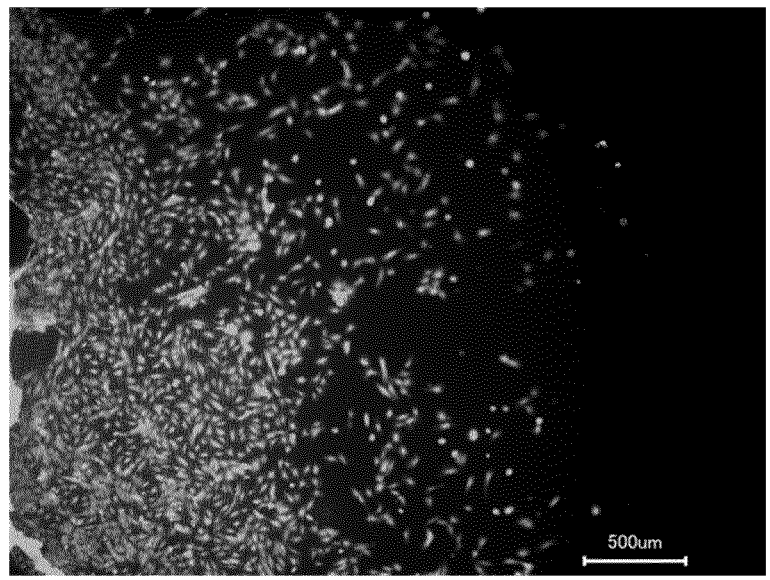
Figure 2B:
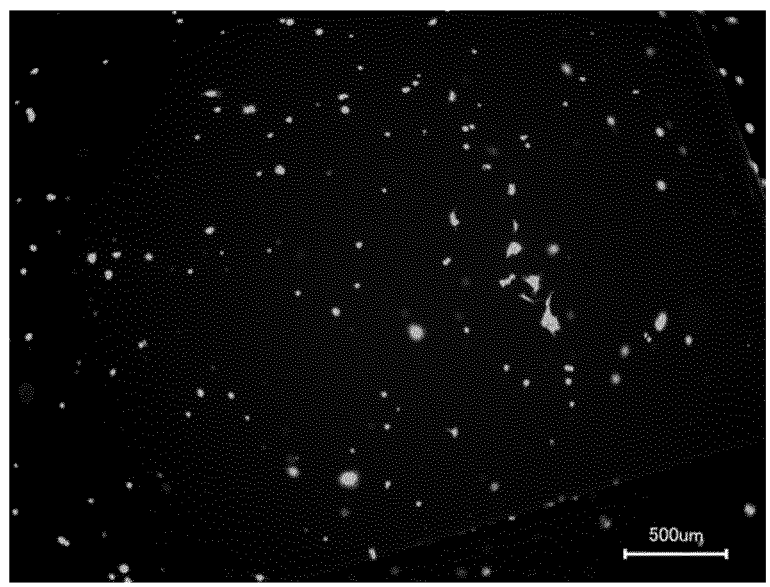

FIG. 2 represents the HUVEC cell adhesion and proliferation on a film prepared from a PAT material having an aliphatic chain of 10 carbon atoms according to a particular embodiment of the present invention (FIGS. 2A and 2C) compared to PET (FIGS. 2B and 2D) at different time intervals (FIGS. 2A and 2B: after 24 h; FIGS. 2C and 2D: after 7 days). The living cells were stained with calcein AM and visualized by a fluorescence Leica microscope, magnification 4×.

Figure 3:
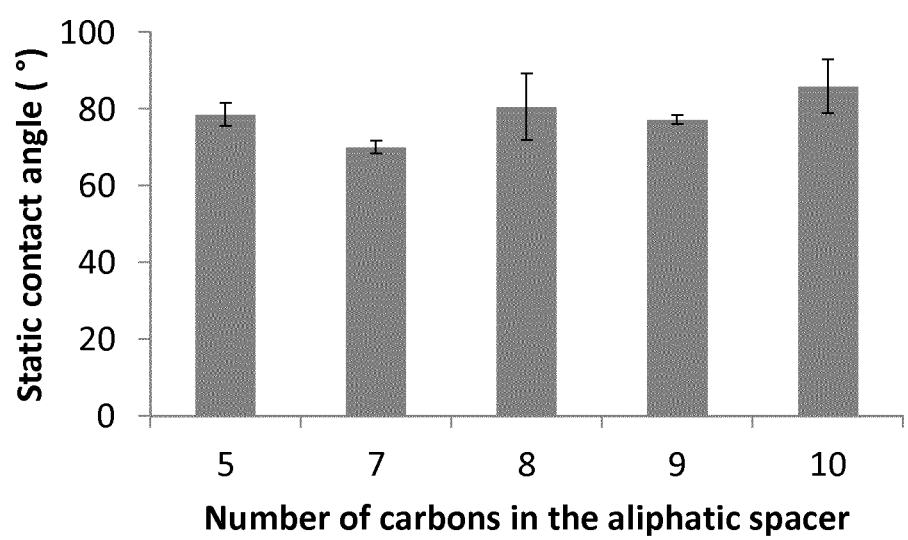

FIG. 3 presents the static contact angle (SCA) values of PAT materials comprising 5, 7, 8, 9 and 10 methylene units in their aliphatic chain according to a particular embodiment of the present invention.

Figure 4:
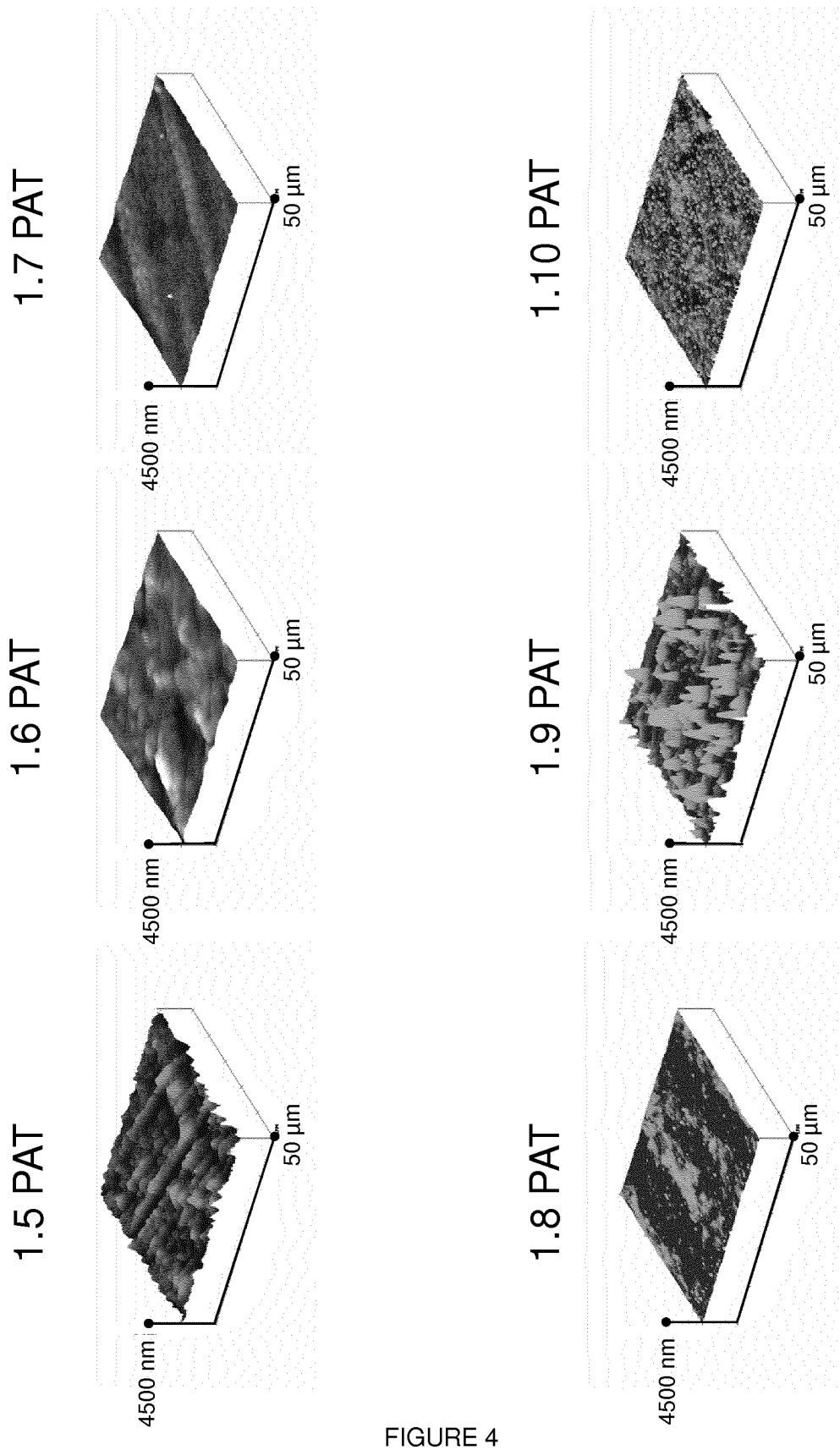

FIG. 4 depicts the surface roughness of PAT materials comprising from 5 to 10 methylene units in their aliphatic chain according to a particular embodiment of the present invention.

Figure 5:
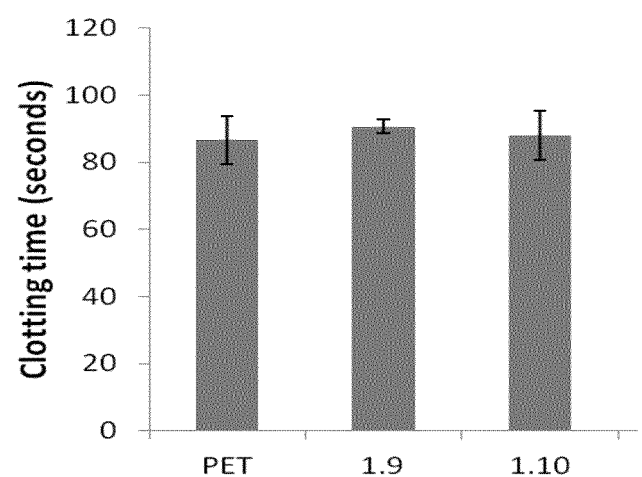
Figure 6A:
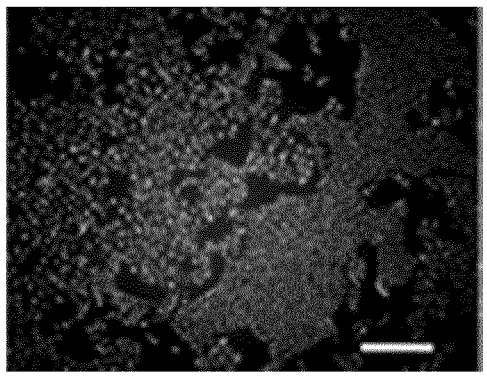
Figure 6B:
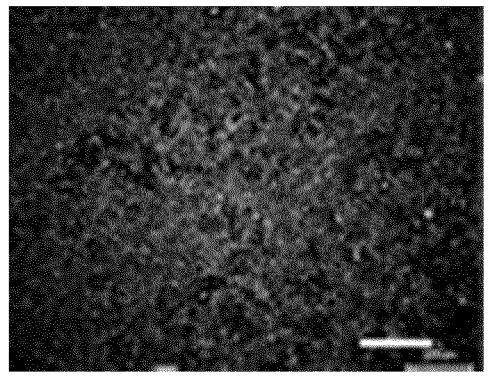
Figure 6C:
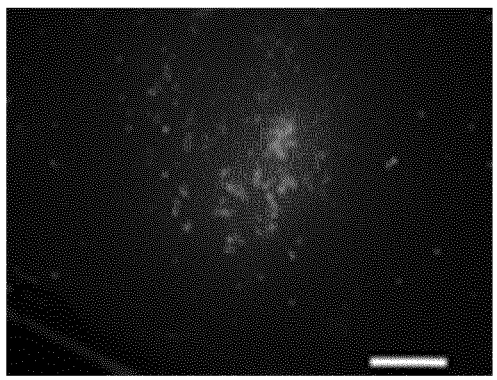
Figure 6D:
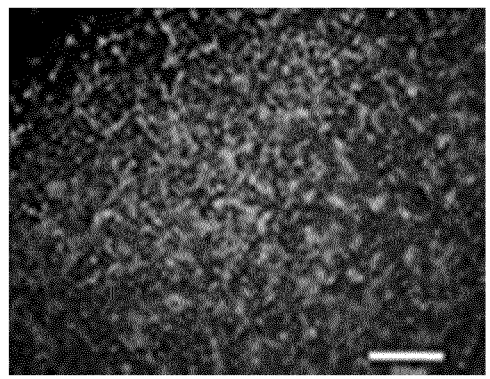

FIG. 5 presents the clotting time required by PAT materials comprising 9 and 10 carbon atoms in their aliphatic chain according to a particular embodiment of the present invention compared with PET.

FIG. 6 represents the HUVEC and HDMEC cell adhesion and proliferation on a film prepared from a PAT material having an aliphatic chain of 9 or 10 carbon atoms according to a particular embodiment of the present invention. The living cells were stained with calcein AM and visualized by a fluorescence Leica microscope, magnification 4×. A cell density of 36 500 cell/cm² was seeded on the polyester film for 24 h. FIG. 6A: HDMEC cells on (1,10) PAT; FIG. 6B: HUVEC cells on (1,10) PAT; FIG. 6C: HDMEC cells on (1,9) PAT; FIG. 6D: HUVEC cells on (1,9 PAT).

DETAILED DESCRIPTION OF INVENTION

Before the present methods and uses of the invention are described, it is to be understood that this invention is not limited to particular methods and uses or combinations described, since such methods and uses and combinations may, of course, vary. It is also to be understood that the terminology used herein is not intended to be limiting. Likewise, in the present description of the invention, reference is made to the accompanying drawings and examples that form a part hereof, and in which are shown by way of illustration only of specific embodiments in which the invention may be practiced. Parenthesized reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the term "number average molecular weight ($M_n$)" relates to the statistical average molecular weight of all the polymer chains in the sample. It is determined by dividing the total weight (mass) of the polymers by the total number of polymers, according to the formula:

$$M_n = \frac{\sum_i N_i M_i}{\sum_i N_i},$$

wherein $M_i$ is the molecular weight of an individual polymer chain and $N_i$ is the number of molecules with molecular weight $M_i$.

As used herein, the term "weight average molecular weight ($M_w$)" takes into account the molecular weight of a polymer chain in determining contributions to the molecular weight average, according to the formula:

$$M_w = \frac{\sum_i N_i M_i^2}{\sum_i N_i M_i}$$

The determination of the number average and weight average molecular weight (mass) of polymers by e.g. gel permeation chromatography or other techniques is well known by the skilled person.

The polydispersity index (PDI) is a measure of the uniformity of the polymer population, or, stated differently, the distribution of molecular weights in a polymer population, and is calculated by the ratio of the weight average to the number average molecular weight ($M_w/M_n$).

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or elements may be combined in any suitable manner, as would be apparent to a person skilled in the art from this disclosure, in one or more embodiments. Furthermore, while some embodiments described herein include some but not other elements included in other embodiments, combinations of elements of different embodiments are meant to be within the scope of the invention, and form different embodiments, as would be understood by those in the art. For example, in the appended claims, any of the claimed embodiments can be used in any combination.

In the following passages, different aspects and embodiments of the invention are defined in more detail. Each aspect and embodiment so defined may be combined with any other aspect/aspects or embodiment/embodiments unless clearly indicated to the contrary. In particular, any feature indicated as being preferred or advantageous may be combined with any other feature/features indicated as being preferred or advantageous.

The inventors have developed improved methods for producing linear aliphatic-aromatic polyesters, in particular poly(alkylene terephthalate) polyesters with long aliphatic chain segments, by performing polyesterification through polycondensation reactions of the respective bifunctional monomers in a solvent. In addition, the inventors have surprisingly found advantageous uses for said poly(alkylene terephthalate) polyesters with long aliphatic chain segments, particularly for selectively growing and/or supporting cell populations, particularly endothelial cell populations.

As used herein, the term "poly(alkylene terephthalate)" or "PAT" refers to polyesters having the structure (A):

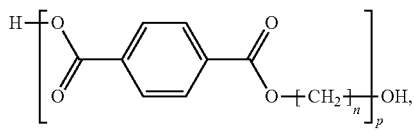

wherein n≥2, preferably n=2 to 20, more preferably n=4 to 20 or n=5 to 20, even more preferably n=4 to 12, 4 to 14 or 4 to 16, most preferably n=5 to 12, such as n=5, 6, 7, 8, 9, 10, 11, or 12; and p≥2, such as p≥3 or p≥10 or p≥20; wherein said polyesters are ester linked polycondensates obtainable from a polycondensation reaction between terephthalic acid (or a derivative thereof) and an aliphatic diol of structure $HOCH_2—(CH_2)_{n-2}—CH_2OH$ (or a derivative thereof), wherein wherein n≥2, preferably n=2 to 20, more preferably n=4 to 20 or n=5 to 20, even more preferably n=4 to 12, 4 to 14 or 4 to 16, most preferably n=5 to 12, such as n=5, 6, 7, 8, 9, 10, 11, or 12. Generally, in a polycondensation reaction, a polymer is formed by condensation reactions between monomers having two functional groups, with the concomitant release of a so-called small molecule (water, methanol, HCl, and the like) as by-product. In the context of the present invention, the condensation reaction is an esterification reaction with the formation of an ester between the organic acid (or a derivative thereof) and the alcohol (or a derivative thereof) and the release of a small molecule. In particularly preferred embodiments, the PAT polyester polymers, product comprising said PAT polyester polymers and uses thereof as envisaged herein, the number (n) of carbon atoms in the aliphatic chain of said PAT polyester polymer having the structure,

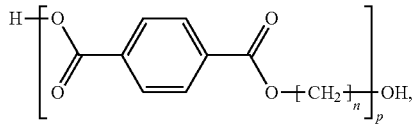

is 5, 6, 7, 8, 9, 10, 11 or 12 and wherein p≥2 preferably with p ranging from 2 or 3 or 10 to 100 or 200 or more, such as p ranging from 5 or 10 to 100 or 200 or more. In preferred embodiments of the products, methods, PAT polyester polymers and uses thereof envisaged herein, the number of carbon atoms in the aliphatic chain (or n) is 5, 7, 9 or 11, preferably wherein n=9. In other preferred embodiments of the products, methods, PAT polyester polymers and uses thereof envisaged herein, the number of carbon atoms in the aliphatic chain (or n) is 4, 6, 8, 10 or 12, preferably wherein n=6, 8, 10 or 12, more preferably wherein n=8 or 10.

Surprisingly, PAT polymers having aliphatic chain segments with 4 or 5 to 20, in particular 4 or 5 to 12, 14 or 16 carbon atoms, preferably with 4 or 5 to 10 carbon atoms, presented cell interaction properties, in particular endothelial cell interactive properties. In contrast, PET presents none or only limited endothelial cell interactive properties. Furthermore, PAT polyesters having aliphatic chain segments with 4 or 5 to 20, in particular 4 or 5 to 12, 14 or 16 carbon atoms, preferably with 5 to 10 carbon atoms present a selective interaction with living cells, in particular with endothelial cells originating from different sources (such as microvascular endothelial cells (e.g. HDMEC) or macrovascular endothelial cells (e.g. HUVEC)) depending on the number of carbon atoms in their aliphatic chain segment of said PAT polymer.

As used herein, a material or substrate with cell interaction or cell interactive properties is in the meaning that said substrate or material has cell adhesion properties, i.e. a material to which a cell can adhere or bind when brought into contact with (a surface of) said material, in such a way that mechanical force or work can be applied to the adhered cell or material without causing the cell and material to separate, and subsequently, allows cell proliferation without phenotype modification of the cell. A material, substrate or product with cell interaction or cell interactive properties is also referred herein as a cell growth support material, substrate or product, i.e. any material, substrate or product allowing the adhesion, migration and/or proliferation of a cell population on said material, substrate or product. Accordingly, materials or substrates to which cells do not adhere do not exhibit cell interactive properties. Cell adhesion can be determined visually by immunostaining fluorescence procedures of specific markers e.g. focal adhesion points, by seeding a cell population on a surface of the material and determining the growth or proliferation of the cells on the material in function of time, such as by visual inspection by a microscope, optionally including the staining of the cells prior to the microscope analysis with calcein AM, or by quantitative techniques e.g. MTT, MTS, Alamar Blue assays etc.

An aspect of the present invention provides a cell growth support product configured for supporting a cell population, preferably an endothelial cell population, comprising a surface for exposure to the cell population during use, wherein said surface comprises a polyester polymer having the structure (A)

(structure A)

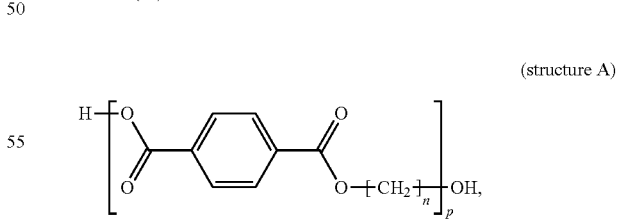

wherein n=4 or 5 to 20, more preferably n=4 or 5 to 12, 4 to 14 or 4 to 16, even more preferably n=5 to 12, such as n=5, 6, 7, 8, 9, 10, 11, or 12; and p≥2, preferably p=3 to 100 or more.

In particular embodiments, said cell growth support product including the surface for exposure to the cell population while in use comprises the polyester polymer having the structure (A) as envisaged herein. Said cell growth support product may thus comprise or be made up of said polyester polymer having the structure (A) as envisaged herein. Alternatively, said cell growth product comprises a surface for exposure to the cell population while in use, said surface comprising the polyester polymer having the structure (A) and said surface being in the form of a coating on said cell growth support product. Advantageously, the polyester according to structure (A) as envisaged herein applied as a coating onto other polymer and metal products favors endothelial cell growth on said polymer or metal products, and/or may allow to introduce specificity towards endothelial cells in said polymer or metal products.

In certain embodiments, the cell growth support product for supporting a cell population as envisaged herein comprises a polyester polymer having the structure (A) wherein n is an even number of carbon atoms, preferably wherein n=4, 6, 8, 10 or 12, particularly wherein n=6, 8, 10 or 12, and wherein said cell population is a macrovascular endothelial cell population, a microvascular endothelial cell population, or a combination thereof. Alternatively, the cell growth support product for supporting a cell population as envisaged herein comprises a polyester polymer having the structure (A) wherein n is an add number of carbon atoms, preferably wherein n=5, 7, 9, or 11, and wherein said cell population is a macrovascular endothelial cell population. Stated differently, the cell growth support product for supporting a cell population as envisaged herein comprises a polyester polymer having the structure (A) wherein n is an odd number of carbon atoms, preferably wherein n=5, 7, 9, or 11, and has selective cell interactive properties within endothelial cell types, favouring adhesion and growth of macrovascular endothelial cells over microvascular endothelial cells.

Said cell growth support product as envisaged herein is suitable for a number of biotechnological and biomedical applications. In certain embodiments, the cell growth support product as envisaged herein is an article, vessel or bioreactor for cell culture applications, such as an array, chip, multi-well plate, or the cell culture chamber (which accommodates the cell culture) of a cell culture device or bioreactor.

In other embodiments, said cell growth support product as envisaged herein is an implantable medical device. The term "implantable medical device" as used herein refers to any product, article or device, which is intended to and configured to be totally or partially introduced into an animal or human body, and which may be used in the treatment and/or assessment of a variety of medical conditions. An implantable medical device as envisaged herein may be introduced into the animal or human body for a short period of time or may be placed therein permanently (e.g. in case of long term implants). For instance, the implantable medical device as envisaged herein may be partly or completely placed into the oesophagus, trachea, colon, biliary tract, urinary tract, vascular system or other location within a human or animal body. In certain embodiments, the implantable medical device as envisaged herein may comprise a medicinal substance, i.e. a pharmacological or therapeutic agent, such as a medicament or a drug, or is configured to comprise, to provide and/or to release, e.g. in a controlled manner, a medicinal substance (also referred to as a drug delivery implantable medical device or an implantable medical device incorporating a medicinal substance or an ancillary medical substance). In certain embodiments, said pharmaceutical or therapeutic agent may assist the function of the implantable medical device. In certain embodiments, said implantable medical device is an implantable medicinal product comprising a pharmaceutical or therapeutic agent, wherein the principal intended action of the implantable medical device is the local delivery of said pharmaceutical or therapeutic agent. Exemplary implantable medical devices as envisaged herein include bypass veins, synthetic vascular grafts, stents, scaffolds, such as tissue engineering scaffolds, orthopaedic implants, and the like. A scaffold is generally a three-dimensional (3D) artificial structure that mechanically and biologically supports the formation of tissue and the growth of cells. Implantable medical devices as envisaged herein may be used in a number of biomedical applications, such as in cardiovascular applications. Particular embodiments relate to the use of the cell growth support product as envisaged herein for the growth, proliferation and/or production of endothelial cells, particularly macrovascular endothelial cells, microvascular endothelial cells or a combination thereof.

Another aspect of the present invention provides for a method for producing the cell growth support product as envisaged herein, said method comprising the steps of obtaining, providing or producing the polyester polymer having the structure (A)

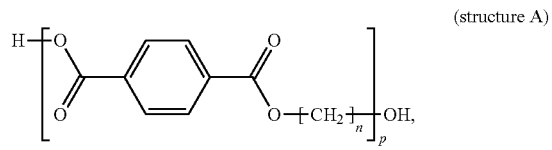

(structure A)

wherein n=4 or 5 to 20, more preferably n=4 to 12, 4 to 14 or 4 to 16, even more preferably n=5 to 20 or 5 to 12, most preferably wherein n=5, 6, 7, 8, 9, 10, 11, or 12; and p≥2, preferably p=3 to 100 or more;
and subsequently forming said polyester polymer into said cell growth support product.

In certain embodiments, the step of obtaining, providing or producing the PAT polyester polymer having the structure (A) comprises preparing said PAT polyester by melt polycondensation of the monomers at high temperatures (about 250° C.) under vacuum conditions, in the presence of catalysts (eg. Ti(OBu)4, tetrabutyltitanate), and optionally adding additives, like heat stabilisers, during the melt polycondensation reaction. Melt polycondensation procedures to obtain PAT polyesters are generally known in the art. In particular embodiments, the step of obtaining, providing or producing the PAT polyester polymer having the structure (A) comprises preparing said PAT polyester via solution polycondensation, wherein the monomers are dissolved in a suitable solvent, according to another aspect of the present invention, as further discussed herein.

Another aspect of the present invention is generally directed to a method for producing linear aliphatic-aromatic polyesters via solution polycondensation. Thus, the present invention also provides a method for producing poly(alkylene terephthalate) polyesters, from aromatic dicarboxylic acids (or an ester-forming derivative thereof, such as an alkyl ester or acyl halide derivative thereof) with aliphatic diols (or an ester-forming derivative thereof) via solution polycondensation, i.e. with the respective bifunctional monomers having two identical functional groups dissolved in a suitable solvent. Advantageously, performing the polycondensation reaction with the bifunctional monomers as envisaged herein yields linear PAT polyesters with high molecular weights and surprisingly low polydispersity index (or PDI), in particular with PDI values ranging between 1.1 and 2.5, such as between 1.3 and 2.4. In contrast, PAT polyesters obtained via melt polycondensation reaction yield PAT polymers with PDI values up to 4.

In particular embodiments, the present invention relates to a method for producing a poly(alkylene terephthalate) polyester polymer having the structure

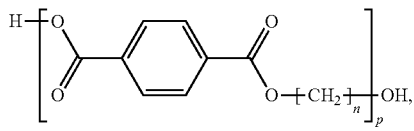

wherein n≥2 or n=2 to 20; preferably, wherein n=4 or 5 to 20, more preferably n=4 or 5 to 12, 4 to 14 or 4 to 16, even more preferably n=5 to 12, such as n=5, 6, 7, 8, 9, 10, 11, or 12; and p≥2, preferably p=3 to 100 or more; and p≥2, preferably with p ranging from 2 or 3 to 200 or more, such as p ranging from 5 or 10 to 100 or 200 or more; comprising the steps of:
(i) mixing a first monomer or compound I having the structure of

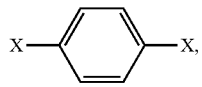

and a second monomer or compound II having the structure of Y—(CH$_2$)$_{n-2}$—Y, wherein n≥2 or n=2 to 20; preferably, wherein n=4 or 5 to 20, more preferably n=4 or 5 to 12, 4 to 14 or 4 to 16, even more preferably n=5 to 12, such as n=5, 6, 7, 8, 9, 10, 11, or 12; in a solvent, thus obtaining a reaction mixture, wherein X and Y are selected to allow the formation of an ester linkage between compound I and compound II and are selected from the functional moieties —COR$^1$ or —CH$_2$OH with R$^1$=—OR$^2$ or a halogen, and R$^2$=H or an alkyl group; and
(ii) allowing a polycondensation reaction to proceed in the solvent, particularly by subjecting the reaction mixture to suitable reaction conditions.

Suitable reactions conditions include, in case of e.g. THF as solvent, at room temperature or under reflux conditions (i.e. 80° C.) or, in case of 1,2 dichlorobenzene as solvent, under reflux conditions (i.e. 160° C.), while vigorously mixing, e.g. for 24 hours or more.

Preferably, when R$^1$ is a halogen, said halogen is chloride or bromide, more preferably, said halogen is chloride.

In certain embodiments, when R$^2$ is an alkyl group, the term "alkyl" refers to a linear or branched carbon chain of between 1 and 20 carbon atoms. In preferred embodiments, the alkyl group is a linear alkyl group comprising between 1 and 8 or 1 and 10 carbon atoms ("C$_1$-C$_8$ alkyl" or "C$_1$-C$_{10}$ alkyl", respectively), more preferably between 1 and 6 or 1 and 4 carbon atoms ("C$_1$-C$_6$ alkyl" or "C$_1$-C$_4$ alkyl", respectively). For instance, C$_1$-C$_{10}$ alkyl includes all linear, or branched alkyl groups having 1 to 10 carbon atoms, and thus includes for example methyl, ethyl, n-propyl, i-propyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers and the like. Preferably, C$_1$-C$_{10}$ alkyl includes all linear alkyl groups having 1 to 10 carbon atoms, and thus includes for example methyl, ethyl, n-propyl, n-butyl, n-pentyl, n-hexyl, n-heptyl, n-octyl, n-nonyl, and n-decyl.

In the context of the present invention, the polycondensation reactions take place with the bifunctional monomers, in casu compound I and II, dissolved in a solvent. Preferably, said solvent is tetrahydrofuran (THF) or 1,2 dichlorobenzene, more preferably said solvent is 1,2 dichlorobenzene. In certain embodiments, chloroform may be used as a solvent.

In particular embodiments of the methods envisaged herein, the concentration of compound I in the reaction mixture is at least 0.05M, more preferably is at least 0.1 M or 0.2M, such as ranging between 0.1 and 2M. In particular embodiments of the methods envisaged herein, the concentration of compound II in the reaction mixture is at least 0.05M, more preferably is at least 0.1M or 0.2M, such as ranging between 0.1 and 2M. In certain embodiments of the methods envisaged herein, the polycondensation (polyesterification) reaction is performed at a molar ratio of compound I to compound II as envisaged herein ranging between 5:1 and 1:5, more preferably ranging between 2:1 and 1:2. Particularly preferred is performing these reactions at about an equimolecular ratio, i.e. about a 1:1 molar ratio of the bifunctional compounds I and II. Advantageously, a 1:1 molar ratio of compound I to compound II yields high quality polymers and promoted the upscaling of the procedure, without affecting the PAT polyester yield.

Preferably, compound I is terephthalic acid, even more preferably compound I is the acyl halide of terephthalic acid, such as terephthaloyl chloride or terephthaloyl bromide, most preferably compound I is terephthaloyl chloride. Advantageously, terephthaloyl chloride has an improved solubility (e.g. in alcohols) compared to terephthalic acid. In addition, using an acyl chloride allows the straightforward removal of the resulting by-product (in casu HCl gas) from the reaction mixture, thus promoting the polycondensation reaction.

In particular embodiments of the methods envisaged herein, compound II is a diol having a linear aliphatic chain with at least 2 carbon atoms, preferably having between 2 and 20 carbon atoms, more preferably having 3, 4, 5, 6, 7, 8, 9, 10, 11, 12, 13, or 14 carbon atoms, such as between 4 or 5 and 12 carbon atoms, even more preferably having between 5 and 10 carbon atoms. In particularly preferred embodiments, compound II is selected from the group consisting of 1,4 butanediol; 1,5 pentanediol; 1,6 hexanediol; 1,7 heptanediol; 1,8 octanediol; 1,9 nonanediol, 1,10 decanediol, 1,11 undecanediol, 1,12 dodecanediol, 1,13 tridecanediol or 1,14 tetradecanediol. Without being bound by theory, the use of these diols result in aliphatic chain segments having 3, 4, 5, 6, 7, 8, 9, 10, 11, 12, 13 or 14, preferably between 4 or 5 and 12, even more preferably between 5 and 10 carbon atoms in the PAT polymer, which increases the flexibility of the polymer compared to PET.

In particular embodiments of the methods envisaged herein, compound II is a compound of structure of Y—(CH$_2$)$_{n-2}$—Y as described herein, wherein said compound II has a linear aliphatic chain with an odd number of carbon atoms and n=2 to 20, preferably n=3 to 14 or 16, more preferably n=4 or 5 to 12. In a particularly preferred embodiment compound II is a diol having an aliphatic chain with an odd number of carbon atoms, such as 1,5 pentanediol; 1,7 heptanediol; 1,9 nonanediol or 1,11 undecanediol.

In other particular embodiments of the methods envisaged herein, compound II is a compound of structure of Y—(CH$_2$)$_{n-2}$—Y as described herein, wherein said compound II has a linear aliphatic chain with an even number of carbon atoms and n=2 to 20, preferably n=3 to 14 or 16, more preferably n=4 or 5 to 12. In a particularly preferred embodiment, compound II is a diol having an aliphatic chain with an even number of carbon atoms, such as 1,6 hexanediol; 1,8 octanediol; 1,10 decanediol or 1,12 dodecanediol.

In particularly preferred embodiments, the present invention relates to a method for producing a poly(alkylene terephthalate) polymer having the structure

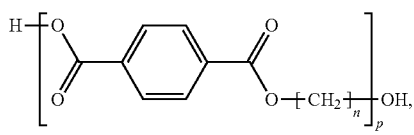

wherein n=4-14, preferably n=5, 6, 7, 8, 9, 10, 11 or 12, even more preferably n=5, 6, 7, 8, 9 or 10; and p≥2, preferably p ranges from 2 or 3 to 100 or 200 or more, more preferably from 3, 5 or 10 to 100 or more, comprising the steps of
(i) mixing terephthaloyl chloride with a linear aliphatic diol comprising between 4 and 14 carbon atoms, preferably a linear aliphatic diol selected from the group consisting of 1,4 butanediol, 1,5 pentanediol; 1,6 hexanediol; 1,7 heptanediol; 1,8 octanediol; 1,9 nonanediol, 1,10 decanediol, 1,11 undecanediol and 1,12 dodecanediol, in 1,2 dichlorobenzene or THF, thus obtaining a reaction mixture, and (ii) allowing polycondensation reaction to proceed, particularly by subjecting the reaction mixture to suitable reaction conditions, preferably reflux conditions under vigorous stirring for 24 hours or more.

In particular embodiments of the methods envisaged herein, an inert, oxygen-free gas is passed through the reaction mixture. Advantageously, in this way the reaction mixture is flushed and the by-product, particularly a gaseous by-product (e.g. HCl, HBr) of the polycondensation reaction can be removed, thus promoting the polycondensation reaction. Exemplary inert gasses include $N_2$, $COO_2$ or noble gasses. Preferably, said inert gas is first passed through the solvent to saturate the inert gas to avoid solvent evaporation. In particular embodiments, the inert gas stream comprising the polycondensation by-product is subsequently treated to remove or neutralize the polycondensation by-product. For instance, with HCl or HBr as by-product, the inert gas may be passed through an alkaline solution, such as a sodium hydroxide solution, to neutralize and capture the gaseous acid.

In certain embodiments of the methods envisaged herein, the by-product of the polycondensation reaction is an acidic by-product, such as HCl or HBr, and is removed by using acid capturing agents, such as TEA, pyridine, . . . It is understood said acid capturing agents may be added to the reaction mixture.

In particular embodiments of the methods envisaged herein, the polycondensation (polyesterification) reaction is performed under mild heating conditions, preferably under reflux conditions, more preferably around 160° C. for 1,2 dichlorobenzene or 80° C. for THF as solvent. Advantageously, reflux conditions (compared with room temperature conditions) promoted the completion of the polyesterification in a shorter period of time and resulted in increased reaction yields, with up to 7 fold efficiency in reaction time and reaction yield.

While in the above passages the methods of the invention are mainly discussed in terms of the preparation and use of poly(alkylene terephthalate) (PAT) polyesters, those skilled in the art are aware that what is described herein can be generalized and applied to preparation of linear aromatic polyesters in a suitable solvent, preferably 1,2 dichlorobenzene or THF, by using aromatic dicarboxylic acids and aliphatic diols in general or compounds derived from aromatic dicarboxylic acids and aliphatic diols which are capable of forming an ester bond ("an ester-forming derivative"). Exemplary compounds of such aromatic dicarboxylic acids include phthalic acid, isophthalic acid, naphthalene dicarboxylic acid, diphenyl dicarboxylic acid, diphenoxyethane dicarboxylic acid and the like. Exemplary compounds of the aliphatic diols to be used include aliphatic diols having the general structure $C_nH_{2n}(OH)_2$, such as an aliphatic diol having the structure HO—$(CH_2)_n$—OH, propylene glycol, and the like, with n as envisaged herein. Ester-forming derivatives of aromatic dicarboxylic acids as envisaged herein include $C_1$-$C_4$ or $C_1$-$C_6$ alkyl esters and phenyl esters of said aromatic dicarboxylic acids, acyl halides, preferably acyl chlorides, of said aromatic dicarboxylic acids or the corresponding diol of said aromatic dicarboxylic acids. Ester-forming derivatives of the aliphatic diols as envisaged herein include monocarboxylic acid esters of said aliphatic diol and the corresponding acyl halide and the like.

The methods envisaged herein allows obtaining PAT polyesters, particularly PAT polyesters with aliphatic chain segments having 4 or 5 to 12, 14 or 16 or 5 to 10 carbon atoms, with bulk properties similar to PET, but having a higher flexibility, as indicated by a lower glass transition ($T_g$) and melting ($T_m$) temperatures compared to PET. Without being bound by theory, the aromatic residues and ester bonds represent stiff points in the polymer chain, which are separated by a flexible aliphatic chain of 4 or 5 to 12, 14 or 16, such as 5 to 10 carbon atoms. The PAT polymers as envisaged herein, particularly PAT polyesters with aliphatic chain segments having 4 or 5 to 12, 14 or 16, such as 5 to 10 carbon atoms, are stable materials having a high degradation temperature (about 380° C. to 410° C. in inert atmosphere and about 360° C. to 400° C. in oxidative conditions), allowing their processing by common industrial thermoforming manufacturing processing methods and equipment, such as by injection molding, drawing and/or extrusion which are performed from molten phase (i.e. at high temperatures, usually much higher than the melting temperature of the to-be-processed polymer). Advantageously, in view of the lower melting temperatures of the PAT polymers as envisaged herein compared to PET, these polymers can be processed under more favorable (temperature) conditions. Advantageously, the temperatures to process the PAT polyesters as envisaged herein can be reduced (compared to PET), implying lower heat consumption and costs. Furthermore, considering the high thermal stability (cfr. degradation temperatures ranging between 300° C. and 400° C.), these materials are sufficiently versatile to become processed under high temperature conditions. Also, similar with PET, these polymers are thermal stable (i.e. in inert conditions) and thermo-oxidative stable (i.e. in oxidative conditions, such as air), allowing their processing in atmospheric condition. These advantageous properties allow the use of the known melt injection installation/equipment used for PET processing to process the PAT polyesters envisaged herein. In addition, as no catalyst is used during the synthesis process, thermal-anomalies (e.g. decreased thermal stability) are avoided, which can occur when minute traces of catalyst remain. Thus, in a second aspect, the present invention relates to PAT polyesters, particularly comprising terephthalic residues ester-bonded to aliphatic chain segments with 4 or 5 to 12, 14 or 16 carbon atoms, preferably with 5 to 10 carbon atoms, as obtainable by the methods envisaged herein, as well as their use in a wide variety of applications.

In particular embodiments, the PAT polyesters with aliphatic chain segments having 4 or 5 to 12, 14 or 16 carbon atoms, preferably with 5 to 10 carbon atoms as obtainable by the methods envisaged herein, are soluble in chloroform. Advantageously, this opens up many possibilities in polymer processing and functionalization which is not possible with PET (particularly as obtained by melt polycondensation), which is insoluble in chloroform and most organic solvents.

In particular embodiments, the PAT polyesters with aliphatic chain segments having 4 or 5 to 12, 14 or 16 carbon atoms, preferably with 5 to 10 carbon atoms as obtainable by the methods envisaged herein, have a thermal degradation temperature in inert conditions (i.e. $N_2$) in the range of about 380° C. to about 420° C., preferably in the range of about 390° C. to about 410° C., with the degradation temperature determined by thermogravimetric analysis (TGA), wherein the weight loss is recorded as a function of temperature under inert atmosphere ($N_2$) at a heating rate of 10° C./min, and wherein the degradation temperature corresponds to the temperature of maximal thermal degradation, or stated differently, the peak temperature of the first derivative of the TGA thermal curve. This indicates the good thermal stability of the polyesters.

In particular embodiments, the PAT polyesters with aliphatic chain segments having 4 or 5 to 12, 14 or 16 carbon atoms, preferably with 5 to 10 carbon atoms as obtainable by the methods envisaged herein, have a (thermo-oxidative) degradation temperature in oxidative conditions (e.g. in air) in the range of about 360° C. to about 410° C., preferably in the range of about 370° C. to about 400° C., with the degradation temperature determined by thermogravimetric analysis (TGA), wherein the weight loss is recorded as a function of temperature in air at a heating rate of 10° C./min, and wherein the degradation temperature corresponds to the peak temperature of the first derivative of the TGA thermal curve.

In particular embodiments, the PAT polyesters with aliphatic chain segments having 4 or 5 to 12, 14 or 16 carbon atoms, preferably with 5 to 10 carbon atoms as obtainable by the methods envisaged herein, have a melting temperature ranging from about 90° C. to about 150° C., depending on the length of the aliphatic chain, with the melting temperature determined by DSC at a heating rate of 10° C./min under nitrogen flow (50 mL/min) and wherein the samples have been prior subjected to a melting and quenching (rapid cooling) step to remove the thermal history of the sample. Generally, melting temperature decreases with increasing length of the aliphatic chain but follows an odd—even trend (with respect to the number of carbon atoms in the aliphatic chain).

In particular embodiments, the PAT polyesters with an even number of carbon atoms in the aliphatic chain as obtainable by the methods envisaged herein, particularly having 4, 6, 8, 10 or 12 carbon atoms, have (a) two melting endotherms in the temperature range of about 115° C. to about 150° C., and (b) present a crystallization peak during cooling at about 75° C. to about 100° C., as determined by DSC (under the conditions as described above).

In particular embodiments, the PAT polyesters with an odd number of carbon atoms in the aliphatic chain as obtainable by the methods envisaged herein, particularly having 5, 7, 9, or 11 carbon atoms, have (a) one melting endotherm in the temperature range of about 90° C. to about 125° C. preceded by a neat intermediate (small) exothermicity prior the melting peaks, (b) do not exhibit a crystallization peak during cooling, and (c) have a glass transition temperature between about −10° C. and +15° C., as determined by DSC (under the conditions as described above). Longer aliphatic chain lengths correspond to lower glass transition temperatures.

In particular embodiments, the PAT polyesters with an odd number of carbon atoms in the aliphatic chain as obtainable by the methods envisaged herein, particularly having 7 or 9 carbon atoms present an amorphous nature with a low content of crystalline phase ranging between 10 and 25%, preferably between 16 and 22%, as determined by wide angle X-ray diffraction (WAXD). In particular embodiments, the PAT polyesters with an even number of carbon atoms in the aliphatic chain as obtainable by the methods envisaged herein, particularly having 6, 8 or 10 carbon atoms, are a crystalline or semi-crystalline material, as determined by WAXD.

In particular embodiments, the PAT polyesters with aliphatic chain segments having 4 to 20, preferably 4 or 5 to 12, 14 or 16 carbon atoms, preferably with 5 to 10 carbon atoms and with an odd number of carbon atoms in the aliphatic chain as obtainable by the methods envisaged herein, particularly having 5 or 9 carbon atoms, present a rough surface after hot embossing, as determined by Atomic Force Microscopy (AFM). In particular embodiments, the PAT polyesters with an even number of carbon atoms in the aliphatic chain as obtainable by the methods envisaged herein, particularly having 6, 8 or 10 carbon atoms, present a smooth surface after hot embossing, as determined by AFM.

In particular embodiments, the PAT polyesters with aliphatic chain segments having 4 to 20 carbon atoms, preferably having 4 or 5 to 12, 14 or 16 carbon atoms, preferably with 5 to 10 carbon atoms as obtainable by the methods envisaged herein but not necessarily limited to these methods, present a hydrophobic surface after hot embossing, with contact angles ranging between 60 to 100°, more specifically between 70 to 85° as determined by Static Contact Angle (SCA) measurements.

Another aspect of the present invention relates to the use of PAT polyesters having aliphatic chain segments with 4 or 5 to 12, 14 or 16 carbon atoms or 5 to 10 carbon atoms, preferably obtainable by the methods envisaged herein but not limited to these methods, for preparing fibers, containers or packaging material or for use in a thermoforming manufacturing process. Another aspect of the present invention relates to the use of PAT polyesters having aliphatic chain segments with 4 or 5 to 12, 14 or 16 carbon atoms or 5 to 10 carbon atoms, preferably obtainable by the methods envisaged herein but not limited to these methods, for medical or biomedical applications.

Accordingly, another aspect of the present invention relates to the use of PAT polyesters having the structure,

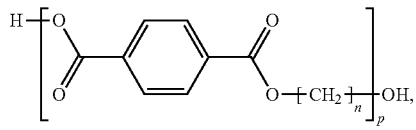

wherein n=4 or 5 to 20, preferably n=4-12, 4-14 or 4-16, 5-12 or 5-10, and p≥2, preferably p ranging from 2 to 100 or more, more preferably p ranging from 3, 4 or 5 to 100 or more, in medical or biomedical applications requiring cell adhesion and cell interaction properties, such as in applications wherein the material has to be integrated within the human body, such as e.g. long term implants. In particular embodiments, said cells adhering to or interacting with said PAT polyesters are endothelial cells, in particular microvascular and/or macrovascular endothelial cells, or stem cells. Said PAT polyesters are preferably obtained by the methods envisaged herein, but may be obtained by other production processes known in the art, e.g. by melt polycondensation. Although PET substrates have a similar hydrophobic surface and surface smoothness properties (after hot embossing) (e.g. SCA of PET is about 73°) as the PAT polyesters having between 4 and 20, particularly between 4 or 5 and 12 or between 5 and 10 carbon atoms in their linear aliphatic chain seqment, PET does not exhibit the excellent cell-interactive properties, in particular towards endothelial cells, of said PAT polyesters.

Particular embodiments relate to the use of PAT polyesters as envisaged herein, particularly having between 4 or 5 and 20 methylene groups in their linear aliphatic chain seqment and having aliphatic chain segments with an even number of carbon atoms, preferably having 4, 6, 8, 10 or 12 carbon atoms, more preferably having 6, 8 or 10 carbon atoms, in medical or biomedical applications requiring cell adhesion and cell interaction properties, particularly in applications requiring the adhesion and interaction with microvascular and/or macrovascular endothelial cells or other types of sensitive cells, such as stem cells. For instance, said PAT polyesters as envisaged herein may be used in implantable medical devices or tissue engineering scaffolds, as discussed above.

Other particular embodiments relates to the use of PAT polyesters as envisaged herein, particularly having between 4 or 5 and 20 methylene groups in their linear aliphatic segment and having linear aliphatic chain segments with an odd number of carbon atoms, preferably having 5, 7, 9, or 11 carbon atoms, more preferably having 5, 7 or 9 carbon atoms, in applications requiring the selective cell adhesion and cell interaction properties favouring adhesion of macrovascular endothelial cells (e.g. HUVEC) over microvascular endothelial cells (e.g. HDMEC).

Accordingly, certain embodiments provide for methods for the separation of microvascular and macrovascular endothelial cells, comprising contacting a mixture of microvascular and macrovascular endothelial cells with a substrate made up of a PAT polyester having between 4 and 20 methylene groups in its linear aliphatic part and having aliphatic chain segments with an odd number of carbon atoms, preferably having 5, 7, 9, or 11 carbon atoms, more preferably having 5, 7 or 9 carbon atoms, and allowing the macrovascular endothelial cells to grow on said PAT substrate.

Furthermore, certain embodiments of the present invention relate to a method for expanding or producing an endothelial cell population, particularly using a cell growth support product as envisaged herein. Accordingly, said method comprises the steps of:
applying endothelial cells, in particular macrovascular endothelial cells (e.g. HUVEC) and/or microvascular endothelial cells (e.g. HDMEC) to a cell growth support product as envisaged herein, particularly a cell growth support product comprising a surface for exposure to the cell population during use, wherein said surface comprises a polyester polymer having the structure (A)

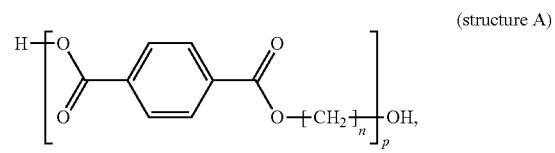
(structure A)

wherein n=4 or 5 to 20, preferably n=4-12 or 5-12; and p≥2, preferably p=3 to 100 or more;
culturing said endothelial cells on said cell growth support product, particularly by applying conditions suitable for cell adhesion and/or cell growth or cell proliferation on said cell growth support product.

The present invention is further illustrated in the following non-limiting examples below.

EXAMPLES

Example 1. Synthesis and Characterization of Poly(Alkylene Terephthalate)s (PAT) by Solution Polycondensation The materials used were terephthaloyl chloride, 1,2 dichlorobenzene (99%, Sigma), chloroform (Chromasolv for HPLC, >99.8%, Sigma), triethyl amine (TEA, Sigma), pyridine (Py, Sigma), 1,6 hexanediol (Sigma Aldrich), 1,9 nonanediol (Sigma Aldrich), 1,10 decanediol (Sigma Aldrich), methanol ($CH_3OH$, 99+%, ChemLab), 1,5 pentanediol (Fluka), 1,7 heptanediol (Acros), 1,8 octanediol (TCl) and deuterated NMR chloroform of 99.8% deuteration degree (Euriso-top).

The synthesis set-up is shown in FIG. 1. In a 3 neck flask equipped with a nitrogen inlet and outlet, equimolar amounts (0.011 moles) of aliphatic diol and terephthaloyl chloride (TCL) were added to 55 mL of 1,2 dichlorobenzene solvent. The aliphatic diols presented various length of the aliphatic chain, having an even or odd number of carbon atoms (n): n=5, 6, 7, 8, 9 and 10. The reaction mixture was heated up to 160° C. and kept under vigorous stirring and reflux for 24 hours. Nitrogen was used as carrier phase to flush out the obtained hydrogen chloride (HCl) during the polycondensation reaction. The inert gas was initially passed through a solvent bath (B) containing dried 1,2 dichlorobenzene and directed through the outlet to a neutralizing bath (C) containing about 200 mL of 4M NaOH solution. The final polymers were obtained after precipitation in cold methanol, filtration and drying in the oven at 50° C. for 48 hours. The final product presented a white colour. A similar procedure was used with THF as solvent, with the reaction performed at 80° C. under reflux conditions.

Polycondensation (in this case a polyesterification) in solution was chosen as synthesis route for the PAT polyesters. The bifunctional monomers, i.e. an acid chloride (here: terephthaloyl chloride (TCL)), and linear alcohols were reacted in 1,2 dichlorobenzene solvent. Terephthaloyl acid chloride was preferred instead of terephthalic acid, mainly due to its improved solubility in alcohols. Another advantage of using an acid chloride is also the straightforward removal of the resulting by-product namely HCl gas. The polycondensation reaction was performed at equimolar amounts of the monomers. Reaction equilibrium was shifted towards completion of the polycondensation reaction by the removal of the gaseous by-product (HCl) through purging procedures. By passing an inert carrier, such as $N_2$, through the reaction mixture, a better homogeneity of the mixture was realized simultaneously with the removal of HCl gas.

This shift in the reaction equilibrium towards polymerisation resulted in high reaction yields (η>60%, see Table 1). The nitrogen and HCl stream was subsequently directed through a NaOH solution, which neutralized the acid. In order to avoid solvent evaporation during purging, a container filled with dried 1,2 dichlorobenzene was placed before the reaction set-up. This way, the nitrogen stream was saturated with solvent before being flushed into the reaction mixture. This promoted the reproducibility of the reaction.

TABLE 1

Overview of PAT polyesters obtained according to embodiments of the method of the present invention

| Sample code | n | Yield (η, %) | Mw (GPC) | PDI (GPC) |
|---|---|---|---|---|
| (1, 5) PAT | 5 | 60 | 12 425 | 2.2 |
| (1, 6) PAT | 6 | 66 | 15 455 | 2.0 |
| (1, 7) PAT | 7 | 70 | 19 195 | 1.8 |
| (1, 8) PAT | 8 | 72 | 12 715 | 1.6 |
| (1, 9) PAT | 9 | 75 | 13 090 | 2.4 |
| (1, 10) PAT | 10 | 72 | 20 015 | 1.9 |

PDI: polydispersity index;
Mw: weight average molecular weight, as determined by gel permeation chromatography (GPC) vs polystyrene standards.
The sample codes refer to aliphatic diol HO—$(CH_2)_n$—OH used, with (1, n) referring to the position of the hydroxyl group and
(n) referring to the number of carbon atoms in the linear aliphatic chain of the diol.

This way, linear aliphatic-aromatic PAT polyesters structurally similar to PET were synthesized starting from an aromatic acid chloride and aliphatic diol as building blocks, corresponding to the following structure wherein n=5, 6, 7, 8, 9 or 10 (alternative to structure A above):

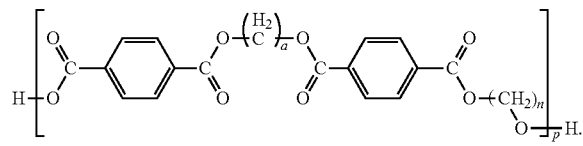

This synthesis procedure was upscaled using 10 and 80 times the amounts of the monomers. The polyester yield was about 70 to 80%, similar to the values presented in Table 1.

Structural characterization was determined by $^1$H-NMR and $^{13}$C-NMR spectroscopy on a Bruker Advance 300 or 500 MHz. The chemical shifts are expressed in ppm (δ) relative to tetramethylsilane (TMS) as internal standard. All spectra are recorded in deuterated chloroform ($CDCl_3$) under ambient conditions.

By comparing the $^1$H-NMR spectra of the monomers (TCL, diols) and the respective aliphatic-aromatic polyesters, the spectra of the novel polyesters were found to be consistent with the expected structure, indicating that no side reaction occurred during the synthesis. Indeed, the shift of the aromatic hydrogen resonance to lower fields, the appearance of a new signal at 4.34 ppm, contributed to the α-methylene hydrogens near the ester moiety, confirmed the polymerization reaction. Furthermore, the proton ratio between α-($CH_2$) (i.e. adjacent to the ester linkage) and the other hydrogen atoms present in the aliphatic chain moieties were calculated and were in line with the theoretical values (e.g. in case of n=9: theoretical ratio H (α-($CH_2$)) to H (non-α-($CH_2$))=1:3.5; experimental value 1:3.66).

In addition, no unreacted monomer, particularly unreacted TCL, was found in the product, indicating completion of the polycondensation reaction and/or the effective removal of any unreacted TCL from the final polymer product.

The $^{13}$C-NMR spectra confirmed the results from the proton NMR spectroscopy and the structure of synthesized PAT polyesters. The presence of quaternary aromatic and carbonyl carbon atoms was demonstrated. The ester group formation was confirmed by the presence of a secondary C atom of the methylene group in a position to the ester bond around 65 ppm and the shift of the aromatic —CH— atoms upfield, from 131.5 ppm in TCL to 129.5 ppm within the polyester.

The NMR data thus clearly show that a variety of polyesters were obtained by the condensation of TCL with 1,5 pentanediol; 1,6 hexanediol; 1,7 heptanediol; 1,8 octanediol; 1,9 nonanediol and 1,10 decanediol, respectively. PAT polymers were synthesized by the successful incorporation of the linear aliphatic chains of different lengths within ester groups and aromatic rings.

Solubility of the polyesters was tested in a wide range of organic solvents and compared with the solubility of PET.

PET and the aromatic polyalkylene polyesters were all insoluble in water and most of the organic solvents tested (toluene, THF, acetone, DMSO, MeOH). This was expected due to the structural similarities of the novel aromatic PAT polyesters with PET, which is soluble only in strong halogenic acids, such as trifluoroacetic acid. The polyesters obtained via solution polycondensation with TCL and the aliphatic diols were also soluble in TFA, but unlike PET, were soluble in chloroform as well.

Average molecular weights of the synthesized polymers were measured by gel permeation chromatographer (GPC) equipped with a differential refractometer detector (Waters 2695, Separation Module). Sample analyzed volume was 20 μL under a 1 mL/min flow rate mobile phase, i.e. chloroform supplemented with 0.2-0.5% triethyl amine (TEA). Monodisperse polystyrene standards (Polymer Laboratories) with 2 960, 7 200, 10 500 and 21 000 Da molecular weights of the highest peak ($M_p$) and narrow polydispersity indexes (PDI<1.2) were used for calibration. Number average molecular weight ($M_n$), weight average molecular weight ($M_w$) and polydispersity indices (PDI) were calculated for each polymer from the standard calibration curve using Mp of the polystyrene standards.

GPC showed that PAT polyesters with weight average molecular weights ranging between 12 000 to 20 000 Da were obtained by solution polycondensation (see Table 1). Interestingly, the polydispersity index obtained was between 1.6 and 2.4, which is a narrow range when considering the applied polymerization method. In melt polycondensation reactions, PDI values as high as 4 can be obtained. Without being bound by theory, in melt polymerization, the mobility of the (macro)molecules is restricted due to viscosity and the polymer degrades due to the high temperatures applied, and therefore a higher variation of polymeric chain length can be formed.

Thermal Analysis

The thermal stabilities of the PAT polymers reported herein were analyzed by thermal gravimetric analysis (TGA) under inert and oxidative atmosphere and calorimetric analysis by differential scanning calorimetry (DSC) and rapid-heating scanning calorimetry (RHC) methods. PET was analyzed in a similar manner as a reference sample. The aim of the thermal analysis was to evaluate the flexibility of the polymers (as seen on their glass transition ($T_g$) and melting (Tm) temperatures). The stability (degradation temperature) is important for the assessment of the industrial applicability. For example, melt injection is the most popular polymer processing method at industrial level and it is performed at high temperatures, usually much higher than the melting temperature of the to-be-processed polymer.

The thermal stability was investigated with a thermogravimetric analysis (TGA, Q50, TA Instruments, Inc.). Samples were heated up at a rate of 10° C./min under constant flow 60 mL/min (balance is stabilized with 40 mL/min) of dispensing gas and the residual weight was recorded as a function of temperature, within 30° C. and 700° C. The 1, 5 and 10% weight loss amounts and the onset point were recorded. To further clarify the thermal behavior, the peak temperature of the TGA trace derivative was recorded as the temperature of maximal degradation ($T_{max}$).

The relative thermal stability of the PAT polyesters was assessed by determining the mass loss in time under inert atmosphere, $N_2$, from thermogravimetric curves and their first-order derivatives. The temperature of maximal degradation ($T_{max}$) was set as the peak value assigned to the first order derivative of the thermogravimetric curve which corresponds to the inflection point of the thermogravimetric curve. All $T_m$ax values and the temperatures at which 1, 5 and 10% weight loss is realized under inert atmosphere are recorded in Table 2. It can be seen that the novel PAT polymers are stable up to 300° C. and decompose by a one-stage weight loss process. A fast degradation rate of all polyesters was noticed. Up to 90 w % of the samples already decomposed in the range of 380° C. to 440° C. and negligible residue remained, less than 1 percent at temperatures higher than 600° C. This behavior was similar to PET, which had a maximum degradation point at about 440° C. ($T_{max}$=442° C.) and presented a one-stage degradation behavior as well.

TABLE 2

TGA results of PAT polyesters obtained according to embodiments of the method of the present invention in inert atmosphere, compared to PET (commercial sample, obtained by melt polycondensation).

| Sample | n | $T_{max, N2}$ (° C.) | T (1% Mass loss) (° C.) | T (5% Mass loss) (° C.) | T (10% Mass loss) (° C.) |
|---|---|---|---|---|---|
| (1, 2) PET | 2 | 442 | 363 | 397 | 408 |
| (1, 5) PAT | 5 | 404 | 342 | 367 | 375 |
| (1, 6) PAT | 6 | 386 | 310 | 348 | 358 |
| (1, 7) PAT | 7 | 403 | 345 | 368 | 377 |
| (1, 8) PAT | 8 | 404 | 360 | 372 | 379 |
| (1, 9) PAT | 9 | 388 | 309 | 348 | 360 |
| (1, 10) PAT | 10 | 404 | 326 | 368 | 379 |

Similar TGA experiments were performed in oxidative conditions (i.e. air) as well. The corresponding thermo-oxidative degradation parameters of the synthesized PAT polymers and PET are shown in Table 3. The degradation curves of studied polyesters in air exhibited a two-stage degradation. The use of an oxidative atmosphere accelerated the decomposition of the materials and shifted the thermogravimetric curves to lower temperatures in comparison to those obtained using inert atmosphere. In contrast with the analysis under nitrogen, the thermo-oxidative decomposition took place through a first step that consumed 90-95% of mass; followed by a second step consuming the entire remaining residue. PET presented a similar behavior of degradation in the presence of oxygen, but with its maximum weight loss in the first stage occurred at higher temperatures ($T1_{maxO2}$ (PET)=430° C.) than investigated PAT compounds.

TABLE 3

TGA results of PAT polyesters obtained according to embodiments of the method of the present invention in air (oxidative) atmosphere, compared to PET (commercial sample, obtained by melt condensation).

| Sample | n | $T1_{max,air}$ (° C.) | $T2_{max,air}$ (° C.) | T (1% Mass loss) (° C.) | T (5% Mass loss) (° C.) | T (10%, Mass loss) (° C.) |
|---|---|---|---|---|---|---|
| (1, 2) PET | 2 | 430 | 506 | 343 | 387 | 397 |
| (1, 5) PAT | 5 | 399 | 502 | 266 | 312 | 336 |
| (1, 6) PAT | 6 | 384 | 464 | 275 | 325 | 345 |
| (1, 7) PAT | 7 | 401 | 539 | 301 | 357 | 372 |
| (1, 8) PAT | 8 | 394 | 516 | 328 | 364 | 375 |
| (1, 9) PAT | 9 | 373 | 498 | 268 | 332 | 352 |
| (1, 10) PAT | 10 | 393 | 533 | 260 | 319 | 353 |

Differential scanning calorimetry (DSC using a Q 2000, TA Instruments, Inc.) was applied in order to determine the thermal transitions correspondinq to the qlass transition and melting temperatures at heating rate of 10° C./min under nitrogen flow (50 mL/min). Up to 8 mg of sample was encapsulated in Tzero Aluminum pans (TA Instruments, Inc) and submitted to multiple heating and cooling cycles. The heating cycle was performed from −50° C. up to 200° C. The melting temperatures ($T_m$) and the glass transition temperature ($T_g$), and the (cold) crystallization temperature ($T_c$) were recorded during the heating or cooling cycle, respectively.

In order to study the influence of chemical structure on the glass transition in the absence of crystallinity, all the polymer samples under investigation were first completely melted and then subjected to a rapid cooling step (quenching). This sample pretreatment also removed sample's thermal history. All DSC values were registered from a $2^{nd}$ heating or cooling cycle, after applying such initial heating and cooling cycle. DSC parameters are indicated in Table 4.

TABLE 4

DSC parameters of PAT polyesters obtained according to embodiments of the method of the present invention, compared to PET (commercial sample, obtained by melt polycondensation)

| Sample | n | $T_g$ (° C.) | $T_m$ (peak 1) (° C.) | $T_m$ (peak2) (° C.) | $T_c$ (° C.) (recrystallization) |
|---|---|---|---|---|---|
| (1, 2) PET | 2 | 75 | — | 256 | — |
| (1, 5) PAT | 5 | 11 | — | 122 | — |
| (1, 6) PAT | 6 | — | 133 | 145 | 98 |
| (1, 7) PAT | 7 | 3 | — | 93 | — |
| (1, 8) PAT | 8 | — | 118 | 131 | 79 |
| (1, 9) PAT | 9 | −3 | — | 90 | — |
| (1, 10) PAT | 10 | — | 115 | 127 | 88 |

As indicated in Table 4, the length of the aliphatic chain played a key role in the thermal properties of the linear aromatic PAT polyesters. In the case of an even number of carbon atoms in the aliphatic chain, two distinctive melting peaks co-existed, which correlates with previously reported (double) melting peaks for aromatic polyesters. A distinctive feature of the even series is the fact that a recrystallization peak appeared in the cooling cycle although a quenching procedure was pursued. The thermal behavior indicates that this PAT material comprised different crystals and after melting, a fast recrystallization occurred. Interestingly, for these PAT polyesters with even number of carbon atoms in the aliphatic chain, the glass transition temperature could not be detected.

The odd-series (i.e. the PAT polyesters having an odd number of C atoms in the aliphatic chain) presented one main melting peak, indicating that one type of crystals forms the majority of the crystals. Also, in this series, a clear glass transition was noticed, which was negatively dependent on the number of carbon atoms (n). PET, as a reference sample, seemed to follow the odd series trend, and not the even series. In addition, PET, like the (1,5) PAT sample exhibited cold crystallization just before melting.

A general decreasing trend of the melting temperature could be observed within both odd and even series of PAT as the number of carbon atoms within the aliphatic chain increased. For the odd series of PAT polyesters $T_g$ decreased with increasing number of carbon atoms in the aliphatic chain, indicating more flexible chains with the longer aliphatic chains.

The melting temperatures of all PAT polyesters present herein are lower than PET. With melting temperatures between 90° C. and 150° C., these polymers can be very suitable candidates for industry as the temperatures required to process them are reduced which also implies lower heat consumption and costs. Interesting, due to the high thermal stability (degradation temperatures ranging between 300° C. and 400° C.), these materials are also versatile to be processed under high temperature conditions, allowing the use of melt injection installations/platforms previously used for PET for the processing of herein presented linear aliphatic-aromatic polyesters.

Rapid heating—cooling calorimetry (RHC) was used in order to gain superior insight into the thermal behavior of the polymers. RHC is a rapid-scanning differential scanning calorimeter DSC prototype, developed by TA Instruments, capable of fast heating and cooling with rates up to 2000° C./min, thereby increasing the sensitivity towards thermal transitions. A fast cooling and heating rate of 500° C./min was utilized in parallel with a 20° C./min cooling rate followed by a 500° C./min heating rate. The fast cooling rate was applied in order to record the $T_g$ more sensitively and to avoid cold crystallization and reorganization. The calibration was performed with indium and tin similar with conventional DSC, but at 500° C./min. Up to 0.3 mg of sample was encapsulated into aluminum crucibles. Similarly with DSC, all values reported were recorded in the second heating cycle (see Table 5).

TABLE 5

RHC parameters of PAT polyesters obtained by solution polycondensation according to embodiments of the method of the present invention, compared to PET (commercial sample, obtained by melt polycondensation)

| Sample | n | $T_g$ (*) (° C.) | $T_m$ (peak) (*) (° C.) | $T_g$ () (° C.) | $T_m$ (peak) () (° C.) |
| --- | --- | --- | --- | --- | --- |
| (1, 2) PET | 2 | 75 | — | 75 | — |
| (1, 5) PAT | 5 | 16.3 | 115 | 15.5 | — |
| (1, 6) PAT | 6 | 23 | 138 | 19 | 138 |
| (1, 7) PAT | 7 | 7 | — | 6 | — |
| (1, 8) PAT | 8 | 9.6 | 114 | 9 | 124 |
| (1, 9) PAT | 9 | 2.7 | 83 | -2.8 | 83 |
| (1, 10) PAT | 10 | 4.5 | 121 | 3 | 123 |

(*) cooling rate: 20° C./min
(**) cooling rate: 500° C./min

Table 5 reports on the $T_g$ and the $T_m$ values obtained by RHC for all PAT materials and PET. As anticipated upon significantly increasing the scanning rate, the $T_g$ values recorded by RHC were higher than the ones recorded by DSC. However, for Tm the opposite was observed. This can most likely be explained by crystal reordering during DSC analysis.

The rather slow heating rates associated with DSC enable the formation of more stable crystals upon heating, leading to a higher $T_m$. The high heating rate used in RHC is avoiding this process. Similar as for DSC, two melting peaks were recorded for (1,6) PAT, (1,8) PAT and (1,10) PAT (i.e. PAT with an even number of carbon atoms in the aliphatic chain) with a small peak at lower temperatures, probably due to secondary crystallization, and the primary crystallization peak at higher temperatures. The relative intensity of the peak at lower temperatures was much lower than observed through DSC. These results indicate that all materials of the even series are also capable of crystallizing when cooled at 500° C./min. Interestingly, this was not the case for the materials of the odd series. (1,5) PAT and (1,7) PAT presented no melting peaks when a fast cooling treatment was applied, indicating that they were quenched by this cooling rate. Nevertheless, (1,9) PAT, the member of the odd series with the largest amount of methylene units, is characterised by a pronounced crystallization during heating, which takes place immediately after the $T_g$. The close proximity of the crystallization peak and the glass transition makes an accurate determination of the $T_g$ difficult. While this material shows faster crystallization kinetics than (1,5) PAT and (1,7) PAT, it still crystallizes significantly slower than the materials of the even series.

Overall, when compared with PET, all PAT polyesters comprising 5 to 10 methylene units within their aliphatic chains presented lower melting and glass transition temperatures, indicating an increase in flexibility.

Crystallinity of the PAT material was evaluated by Wide angle X-ray Diffraction (WAXD) analysis using a diffractometer D5000 (Bruker) Bragg Brantano with the following configuration—Anode: Cu (1.5406 Å) 40 KV and 40 mA; the 2 theta range 5°-40° 2 theta; step size 0.02°; time per step 10 s; Graphite monochromator; scintillation detector. The spectra show that the odd PAT samples (n=7 and 9) present an amorphous spectrum, while the even series (n=6, 8 and 10) show a more crystalline structure as evidenced by the recorded sharp peaks.

Example 2. Biological Relevance of the PAT Polyesters

Figure 2C:
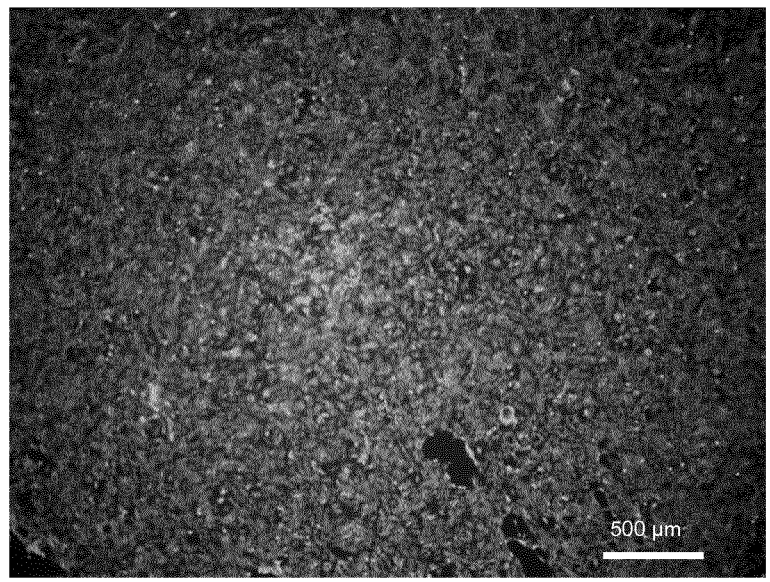
Figure 2D:
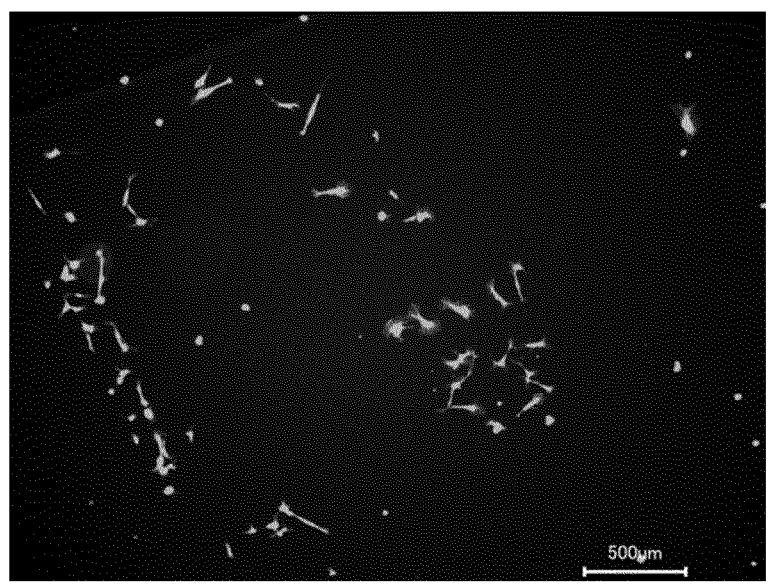

Human umbilical vein endothelial cells (HUVEC) and human dermal microvascular cells (HDMEC) cells with a density of 20 000 cells/mL (passage 2 or 3) were seeded on sterile films of PET and of (1,9) PAT and (1,10) PAT by drop seeding method. At different periods of time (after 24 h and 7 days), the living cells were stained with calcein AM and visualized by a fluorescence Leica microscope, magnification 4×. HUVEC cells adhered well to both the (1,10) PAT and (1,9) PAT films, with a completely overgrown PAT film after 7 days (FIGS. 2A and 2C, for HUVEC). In contrast, only a small number of cells could be detected on the PET film, even after 7 days of incubation (FIGS. 2B and 2D). In addition, HDMEC cells only adhered well to the (1,10) PAT film, while this was not the case for the (1,9) PAT and the PET films. Furthermore, using a similar setup, it was found that other cell types, such as osteoblasts, smooth muscle cells and immortalized L929 fibroblasts formed a confluent cell layer on the (1,10) PAT film.

Accordingly, a clear differentiation between the endothelial cell types (HUVECs versus HDMECs) was observed when seeded on (1,9) PAT polyesters. Although both types of endothelial cells are viable on the "even" (1,10) PAT (see FIGS. 6A and 6B), the "odd" polyester [(1,9) PAT] presented a confluent layer of HUVECs (see FIG. 6D) while few-to-none HDMECs adhered on its surface (see FIG. 6C).

This indicates that the PAT polyesters presented herein have cell-interactive properties which allow the adhesion and proliferation of various types of endothelial cells, specifically depending on the number of carbon atoms in the aliphatic chain. In particular, PAT polyesters having an odd number of C atoms in the aliphatic chain (n=5, 7 or 9) present selectivity towards macrovessel originated endothelial cells (e.g. HUVECs) compared with microvessel originated endothelial cells (HDMEC), while the PAT polyesters having an even number of carbon atoms in the aliphatic chain (n=4 to 10) interact with both types of endothelial cells (e.g. HUVECs and HDMECs).

The excellent cell-interactive properties towards endothelial cells presented by the PAT polymers with different number of methylene groups in the aliphatic chain compared with PET are even more surprising when considering their similar hydrophobic nature (FIG. 3) and the various surface roughness presented by the PAT polymers (FIG. 4). In this context, hydrophobicity and a high roughness of a surface generally result in cell-repealing properties instead of cell-adhesion properties.

The hydrophobic properties of the PAT materials were assessed by measuring the static contact angle (SCA) of a water droplet on the material. Surface wettability was determined by sessile drop method, using a double distilled water drop (1 μL). The drop spreading was imaged using a 25 frames/s video camera and the SCA value was determined using the imaging software provided by the supplier (SCA 20, version 2.1.5 build 16).

Sample roughness was investigated by atomic force microscopy (AFM) measurements using a multimode scanning microscope (Digital Instruments, USA) equipped with a Nanoscopellla controller. Scan sizes of 50 μm×50 μm of 4500 nm height (OZ axis) were acquired in "tapping" mode under ambient conditions using a silicon cantilever (OTESPA, Veeco). Nanoscope software version 4.43r8 was used to obtain the topographical surface from the recorded images after an XY Plane Fit Auto correction and flattening procedure.

No cytotoxicity was presented by the PAT polyesters presented herein as determined by indirect contact method on a fibroblasts L929 cell line (following the guidelines of ISO standard 10993) or on more sensitive primary endothelial cells (e.g. HUVECs). (1,9) PAT and (1,10) PAT films were incubated in cell culture medium for 1, 7 or 14 days. Samples were taken from each supernatant at the mentioned time points and placed in direct contact with a confluent layer of fibroblasts or HUVECs previously seeded on a tissue culture plate. After 24 hours exposure, cell viability was evaluated by MTS assay. An insignificant number of cells died as a result of these tests, the main majority showing no negative response to the added supernatant. The obtained results confirmed the lack of any leakages of toxic compounds such as unreacted monomers or solvent residues. Minute traces of these would have resulted in the death of the cells, especially of the endothelial cells.

In addition, the PAT polyesters presented herein, in particular (1,9) PAT and (1,10) PAT, presented clotting times similar with that of PET as shown in FIG. 5. Clotting tests were performed in platelet-poor plasma isolated from whole human blood freshly harvested from a healthy donor for research purposes only.

Thus, overall, no toxicity, immunogenic or bacterial contamination were observed neither for "odd" or "even" PAT polyesters as envisaged herein; and a clotting time similar with that of PET (the reference material) was observed for both. Surprisingly, both the "odd" and "even" PAT films enabled unexpected cell interactivity towards endothelial cells, allowing cell adhesion and proliferation. What is more, a different behavior towards micro- and macro-origin endothelial cells (cfr. HDMECs versus HUVECs, respectively) was recorded between the odd and even polymer counterpart.

Example 3. Processing Capacity and Industrial Potential

The ability to process the PAT polyesters presented herein into films, filaments and fibers was determined by applying a thermoforming-based technique (e.g. hot embossing), an extrusion-based technique (e.g. plotting from melt) and a speciallized method predominantly applied within the medical field (e.g. electrospinning) Hot embossing/Compression molding experiments were carried out using a Carver Manual Hydraulic Press 12 tone with heated plates (Model 12-12H) in order to obtain flat polymer films. Each of the synthesized polymers was initially melted on a PDMS flat slab and then sandwiched with another PDMS slab. The assembly was placed inside the Carver press at a higher temperature than the polymers' melting temperature (30° C. higher than $T_m$) and held under a pressure of 18 psi for 5 minutes. After removal from the press, the assembly was left to cool down at room temperature. Flexible, stable, opaque, flat films were obtained.

Overall, similar molecular weights and thermal properties were obtained for the processed PAT polyesters as envisaged herein via the compression molding technique, thus indicating the suitability of this processing technique. Noteworthy to mention herein is that industrially available PET granules (Sigma Aldrich) were also used in an attempt to produce films through compression molding. Nevertheless, this was not possible, most likely because of the high Tg value that PET presents (cfr. Tg~78° C.) compared with PDT (with a Tg=5° C.).

Bioplotting. Polymer filaments extruded from melt at a temperature with 30° C. to 40° C. higher than the melting point (e.g. 170° C. for (1,10) PAT) resulted in the fabrication of three-dimensional shapes or scaffolds using a Bioscaffolder@ device (Sys-Eng, Germany). Porous scaffolds of 2 mm height and 10×10 mm² surface and with a 0/90° laydown pattern were thus obtained. The polyester scaffolds were flexible, but maintained their structural integrity given by plotting. What is more, no shrinkage of the scaffolds was observed and the interconnectivity of the pores was preserved, as deducted through visual inspection.

Micro- and nanofibers obtained by electrospinninq. An in house-made electrospinning device was used to electrospun PAT polymers, in particular (1,10) PAT from a 10% (w/v) polymer and 0.5% PEO (w/w, Mw=2 000 000 Da) solution dissolved in $CHCl_3$ and 2-3 drops of trifluoroacetic acid. The polymer solution was placed into a 10 mL syringe, dispensed from a 30 cm distance from the collector, under a 18 kV voltage and at various feed rates, 0.5 mL/h or 2 mL/h. Micro- and nano-metric fibers were obtained. This was possible only as a result of the increased solubility of the PAT polymers in chloroform that ensured safer working conditions compared with the highly toxic and corrosive conditions required for PET (e.g. electrospining of PET is performed from trifluoroacetic acid and dichloromethane solvent mixtures).

Thus, while the melting temperature of 260° C. can be seen as limiting the processing possibilities of PET to those processing techniques able to sustain such high temperatures, the lower melting temperature of the PAT polyesters allowed more versatile processing techniques. The PAT polyesters as envisaged herein could be successfully processed into flat thin films, 3D scaffolds, filaments and fibrous mats by compression molding, bioplotting and electrospinning techniques, respectively.

The invention claimed is:

1. A cell growth support product for supporting a cell population, comprising a surface for exposure to the cell population during use, wherein said surface of said cell growth support product has cell adhesion properties and wherein said surface comprises a polyester polymer having the structure (A)

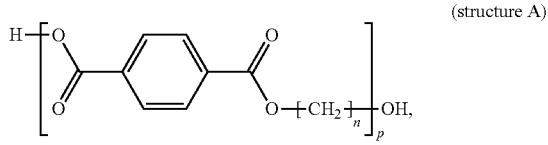

(structure A)

wherein n=5-20; and p≥2.

2. The cell growth support product of claim 1, wherein n=5-12 and p=3 to 100 or more.

3. The cell growth support product of claim 2 wherein n=6, 8, 10 or 12 and wherein said cell population is a macrovascular endothelial cell population, a microvascular endothelial cell population, or a combination thereof.

4. The cell growth support product of claim 2 wherein n=5, 7, 9, or 11 and wherein said cell population is a macrovascular endothelial cell population.

5. The cell growth support product of claim 1 wherein said cell growth support product and said surface thereof comprises the polyester polymer having the structure (A).

6. The cell growth support product of claim 1 wherein said surface comprising the polyester polymer having the structure (A) is in the form of a coating on said cell growth support product.

7. The cell growth support product of claim 1 wherein said product is an article, vessel or bioreactor for cell culture applications.

8. The cell growth support product of claim 1 wherein said product is an implantable medical device.

9. A method for producing the cell growth support product of claim 1, comprising the steps of obtaining or producing the polyester polymer having the structure (A)

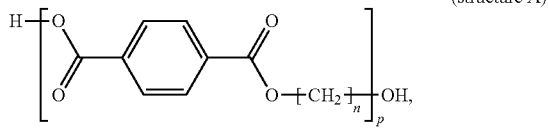

(structure A)

wherein n=5-20;
and p≥2;
and subsequently forming said polyester polymer into said cell growth support product.

10. The method according to claim 9 wherein n=5-12; and p=3 to 100 or more.

11. The method according to claim 9, wherein the step of producing the polyester polymer comprises the steps of:
(i) mixing a first compound I having the structure of

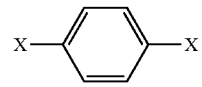

and a second compound II having the structure of Y—(CH2)$_{n-2}$—Y, wherein n=5-20, in a solvent, thus obtaining a reaction mixture, wherein X and Y are selected to allow the formation of an ester linkage between compound I and compound II and are selected from the functional moieties —COR$^1$ or —CH$_2$OH; wherein R$^1$=—OR$^2$ or a halogen; and R$^2$=H or an alkyl group; and
(ii) allowing a polycondensation reaction to proceed in the solvent.

12. The method according to claim 11 wherein the solvent is 1,2-dichlorobenzene or tetrahydrofuran.

13. The method according to claim 11 wherein an inert gas is passed through the reaction mixture during the reaction step (ii).

14. The method according to claim 11 wherein compound II has the structure HOCH$_2$—(CH$_2$)$_{n-2}$—CH$_2$OH and/or wherein compound I has the structure

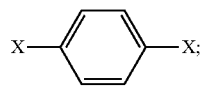

wherein X=—COR$^1$; R$^1$=—OR$^2$ or a halogen, and R$^2$=H or an alkyl group.

15. The method according to claim 14 wherein compound I is terephthaloyl chloride and wherein the compound II is 1,5 pentanediol, 1,6 hexanediol, 1,7 heptanediol, 1,8 octanediol, 1,9 nonanediol or 1,10 decanediol.

16. A method for expanding an endothelial cell population comprising:
applying endothelial cells to a cell growth support product according to claim 1;
culturing said endothelial cells on said product by applying conditions suitable for cell growth or cell proliferation.

17. The method according to claim 16 wherein said endothelial cell population comprises macrovascular endothelial cells, microvascular endothelial cells, or a combination thereof.

18. A method for separating macrovascular and microvascular endothelial cells comprising contacting a cell population comprising macrovascular and microvascular endothelial cells with a cell growth support product according to claim 1, wherein n=5, 7, 9, or 11, and whereby said support product favours adhesion and growth of the macrovascular endothelial cells over the microvascular endothelial cells.

19. The cell growth support product according to claim 7, wherein said product is an array, chip or multi-well plate.

20. The cell growth support product according to claim 8, wherein said product is a synthetic vein or vascular graft, or a tissue engineering scaffold.

* * * * *